US009005248B2

(12) United States Patent
Taber et al.

(10) Patent No.: US 9,005,248 B2
(45) Date of Patent: Apr. 14, 2015

(54) TELESCOPING INTERSPINOUS FIXATION DEVICE AND METHODS OF USE

(71) Applicant: Lanx, Inc., Broomfield, CO (US)

(72) Inventors: Justin Taber, Lafayette, CO (US); Patrick Hunt, Denver, CO (US); Andrew Lamborne, Golden, CO (US); Randall G. Mast, Denver, CO (US); William Sandul, Broomfield, CO (US); Dean Karahalios, Lake Forest, IL (US)

(73) Assignee: Lanx, Inc., Broomfield, CO (US)

( * ) Notice: Subject to any disclaimer, the term of this patent is extended or adjusted under 35 U.S.C. 154(b) by 118 days.

(21) Appl. No.: 13/734,773

(22) Filed: Jan. 4, 2013

(65) Prior Publication Data

US 2013/0184754 A1 Jul. 18, 2013

Related U.S. Application Data

(60) Provisional application No. 61/583,219, filed on Jan. 5, 2012.

(51) Int. Cl.
*A61B 17/70* (2006.01)
(52) U.S. Cl.
CPC ......... *A61B 17/7064* (2013.01); *A61B 17/7068* (2013.01); *A61B 17/7065* (2013.01)
(58) Field of Classification Search
CPC .................................. A61B 17/7068
USPC ........................ 606/246, 248, 249
See application file for complete search history.

(56) References Cited

U.S. PATENT DOCUMENTS

| 7,727,233 | B2 | | 6/2010 | Blackwell et al. | |
|---|---|---|---|---|---|
| 7,776,091 | B2 | | 8/2010 | Mastrorio et al. | |
| 8,048,118 | B2 | * | 11/2011 | Lim et al. | 606/249 |
| 8,241,330 | B2 | * | 8/2012 | Lamborne et al. | 606/248 |
| 8,246,656 | B2 | * | 8/2012 | Ramsay et al. | 606/249 |
| 8,574,267 | B2 | * | 11/2013 | Linares | 606/249 |
| 8,613,758 | B2 | * | 12/2013 | Linares | 606/249 |
| 8,636,773 | B2 | * | 1/2014 | Stern et al. | 606/249 |
| 2008/0167655 | A1 | * | 7/2008 | Wang et al. | 606/90 |
| 2008/0177306 | A1 | * | 7/2008 | Lamborne et al. | 606/246 |
| 2008/0183211 | A1 | * | 7/2008 | Lamborne et al. | 606/249 |
| 2008/0215058 | A1 | * | 9/2008 | Zucherman et al. | 606/90 |
| 2009/0088800 | A1 | * | 4/2009 | Blain et al. | 606/246 |
| 2010/0036419 | A1 | | 2/2010 | Patel et al. | |
| 2010/0087860 | A1 | | 4/2010 | Chin et al. | |
| 2010/0106190 | A1 | * | 4/2010 | Linares | 606/249 |
| 2010/0241167 | A1 | | 9/2010 | Taber et al. | |

(Continued)

OTHER PUBLICATIONS

International Application No. PCT/US2013/020369, International Search Report and Written Opnion, 17 pages, mailed Jul. 18, 2013.

*Primary Examiner* — Eduardo C Robert
*Assistant Examiner* — Jacqueline Johanas
(74) *Attorney, Agent, or Firm* — Harness, Dickey

(57) ABSTRACT

The present invention provides spinous process implants and associated methods. In one aspect of the invention, the implant includes at least one extension with a first part and a second part where at least one arm is coupled to each of the first part and the second part. The first part and the second part are movable from a compact to a distracted state. In another aspect, the present invention provides a second extension that is slidingly coupled to the first and second arms. The second extension further comprises a third part and a fourth part that move with the first and second part.

22 Claims, 24 Drawing Sheets

(56) References Cited

U.S. PATENT DOCUMENTS

| | | |
|---|---|---|
| 2010/0274287 A1 | 10/2010 | Rouleau et al. |
| 2011/0022090 A1 | 1/2011 | Gordon et al. |
| 2011/0054531 A1 | 3/2011 | Lamborne et al. |
| 2011/0066186 A1 | 3/2011 | Boyer, II et al. |
| 2011/0144692 A1 | 6/2011 | Saladin et al. |
| 2011/0160772 A1* | 6/2011 | Arcenio et al. ............... 606/248 |
| 2011/0166600 A1 | 7/2011 | Lamborne et al. |
| 2011/0172709 A1 | 7/2011 | Lyons et al. |
| 2011/0218572 A1 | 9/2011 | Lechmann et al. |
| 2011/0224731 A1 | 9/2011 | Smisson, III et al. |
| 2011/0313458 A1* | 12/2011 | Butler et al. ................... 606/249 |
| 2011/0319936 A1 | 12/2011 | Gordon et al. |
| 2012/0016418 A1* | 1/2012 | Chin et al. ..................... 606/249 |
| 2012/0109202 A1* | 5/2012 | Kretzer et al. ................. 606/248 |
| 2013/0012996 A1* | 1/2013 | Zamani et al. ................. 606/248 |
| 2013/0103088 A1* | 4/2013 | Karahalios et al. ........... 606/248 |
| 2013/0184754 A1* | 7/2013 | Taber et al. .................... 606/249 |
| 2013/0296939 A1* | 11/2013 | Perkins ........................ 606/249 |

* cited by examiner

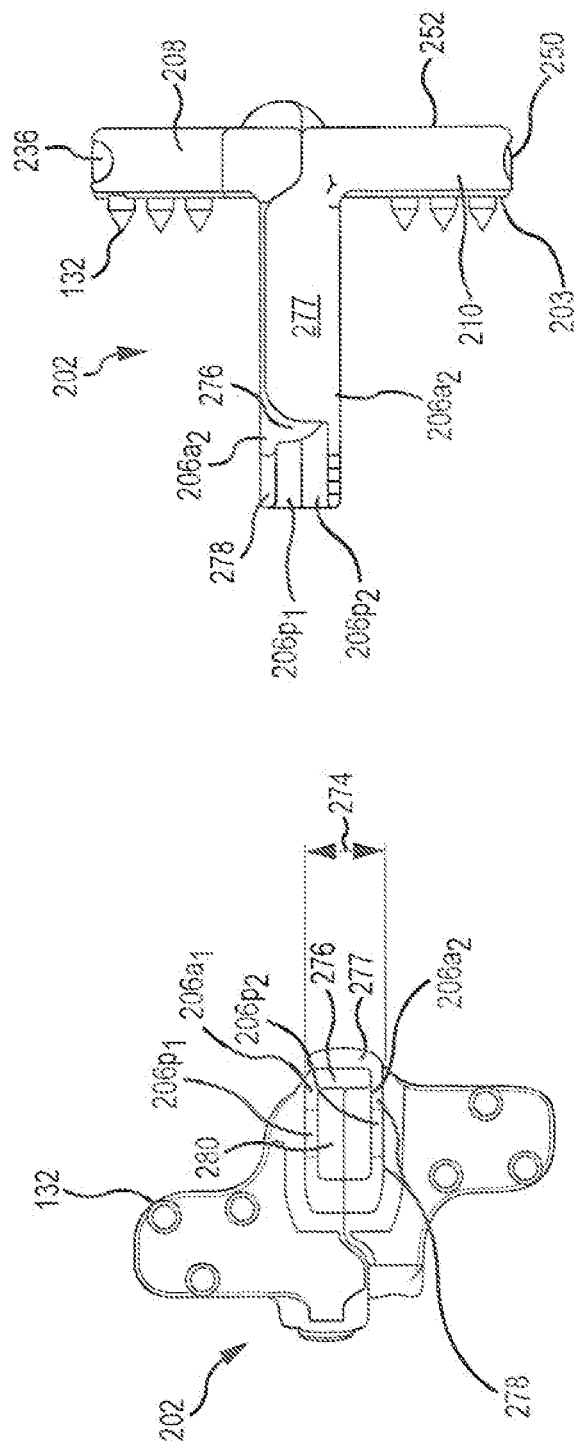

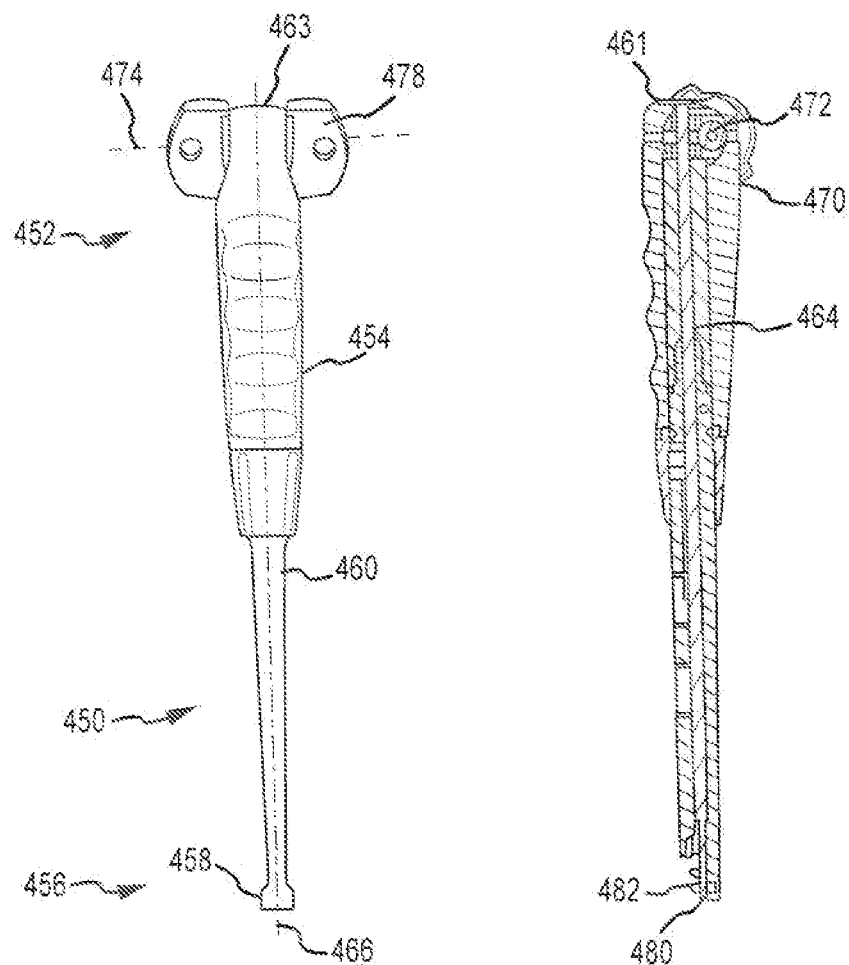

TELESCOPING INTERSPINOUS FIXATION DEVICE AND METHODS OF USE

PRIORITY

This application claims priority under 35 U.S.C. §119 to U.S. Provisional Patent Application Ser. No. 61/583,219, filed Jan. 5, 2012, titled Telescoping Interspinous Fixation Device and Methods of Use, which is incorporated herein by reference as if set out in full.

CROSS-REFERENCE TO RELATED APPLICATIONS

This application is related to U.S. patent application Ser. No. 11/934,604, filed Nov. 2, 2007, titled Spinous Process Implants and Associated Methods, now U.S. Pat. No. 8,241,330; U.S. patent application Ser. No. 12/020,282, filed Jan. 25, 2008, titled Spinal Implants and Methods; U.S. patent application Ser. No. 12/751,856, filed Mar. 31, 2010, titled Spinous Process Implants and Associated Methods; U.S. patent application Ser. No. 12/538,710, filed Aug. 10, 2009, titled Spinous Process Implants, Instruments, and Methods; and U.S. patent application Ser. No. 12/854,125, filed Aug. 10, 2010, titled Interspinous Implants and Methods; U.S. patent application Ser. No. 13/460,738, filed Apr. 30, 2012, titled Spinous Process Implants and Associated Methods; and U.S. patent application Ser. No.; and U.S. patent application Ser. No. 13/584,661, filed Aug. 13, 2012, titled Spinous Process Implants and Associated Methods; all of which are incorporated herein by reference as if set out in full.

FIELD

The technology of the present application relates to spinal implants and, more specifically, to an interspinous implant for fixation to one or more spinous processes of a spine.

BACKGROUND

The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist. With age or injury, spinal discs begin to break down, or degenerate, resulting in the loss of fluid in the discs, and consequently, the discs become less flexible. Likewise, the discs become thinner allowing the vertebrae to move closer together. Degeneration also may result in tears or cracks in the outer layer, or annulus, of the disc. The disc may begin to bulge outwardly. In more severe cases, the inner material of the disc, or nucleus, may actually extrude out of the disc. In addition to degenerative changes in the disc, the spine may undergo changes due to trauma from automobile accidents, falls, heavy lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed leading to pressure on the nerve tissue which can cause pain, numbness, weakness, or even paralysis in various parts of the body. Finally, the facet joints between adjacent vertebrae may degenerate and cause localized and/or radiating pain. All of the above conditions, as well as others not specifically mentioned, are collectively referred to herein as spine disease.

Conventionally, surgeons treat spine disease by attempting to restore the normal spacing between adjacent vertebrae. This may be sufficient to relieve pressure from affected nerve tissue. However, it is often necessary to surgically remove disc material, bone, or other tissues that impinge on the nerve tissue and/or to debride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of bone plates and/or pedicle screws fastened to the adjacent vertebrae.

Although techniques for placing intervertebral spacers, plates, and pedicle screw fixation systems have become less invasive in recent years, they still require the placement of hardware deep within the surgical site adjacent to the spine. Recovery from such surgery can require several days of hospitalization and long, slow rehabilitation to normal activity levels.

Rather than spinal fusion, investigators have promoted the use of motion preservation implants and techniques in which adjacent vertebrae are permitted to move relative to one another. One such implant that has met with only limited success is the artificial disc implant. The artificial disc typically includes either a flexible material or a two-piece articulating joint inserted in the disc space. Another such implant is the spinous process spacer which is inserted between the posteriorly extending spinous processes of adjacent vertebrae to act as an extension stop and to maintain a minimum spacing between the spinous processes when the spine is in extension. The spinous process spacer allows the adjacent spinous processes to move apart as the spine is flexed. The extension stop spacers, however, also have had limited success.

Recently, the trend has been back towards fusion devices rather than motion preservation devices. One promising recent implant is a spinal process fusion plate. Similar to the fusion implants, the spinal process fusion plate promotes fusion between adjacent vertebrae to relieve pressure on the nerve. However, unlike more conventional spinal implant systems, the spinal process fusion plate facilitates less invasive procedures than conventional spinal fusion surgery. The need still exists for improved spinal process fusion plates to facilitate even less invasive surgery including, minimally invasive surgery, percutaneous implantation, and the like. Such less invasive surgery may be accomplished by an implant that may be implanted in a more compact or relatively compact state and expanded or enlarged state.

BRIEF DESCRIPTION OF THE DRAWINGS

Various examples of the technology of the present application will be discussed with reference to the appended drawings. These drawings depict only illustrative examples of the technology described more fully herein and are not to be considered limiting of its scope.

FIG. 16 is a view of a part of the implant;

FIG. 17 is a view of a part of the implant;

FIGS. 34-40 are view of tools usable with the technology of the application.

DESCRIPTION OF THE ILLUSTRATIVE EXAMPLES

Figure 1:
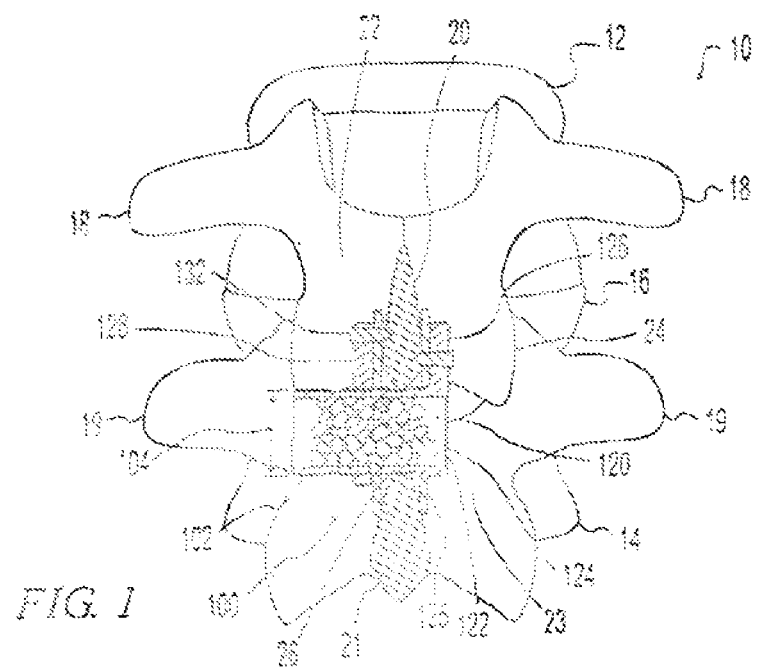
FIG. 1 is a posterior cross sectional view of an implant in situ that is deployed using a tool consistent with the technology of the present application.

The technology of the present application will be described in the context of spinal surgery, but one of ordinary skill in the art will recognize on reading the disclosure that the technology may be applicable to other medical fields. Moreover, the technology of the present application will be described with reference to certain exemplary embodiments. The word "exemplary" is used herein to mean "serving as an example, instance, or illustration." Any embodiment described herein whether or not specifically identified as "exemplary" is not to be construed as preferred or advantageous over other embodiments. It also should be understood that terminology employed herein is used for the purpose of describing particular embodiments only and is not intended to be limiting. It must be noted that, as used in this specification, the singular forms "a," "an," and "the" include plural references unless the context of the disclosure clearly dictates otherwise. Thus, for example, reference to "a lithium hydroxide" is not to be taken as quantitatively or source limiting, reference to "a step" may include multiple steps, reference to "producing" or "products" of a reaction should not be taken to be all of the products of a reaction, and reference to "reacting" may include reference to one or more of such reaction steps. As such, the step of reacting can include multiple or repeated reaction of similar materials to produce identified reaction products.

Further, the instrument(s) described in accordance with the technology of the present application facilitate surgical implantation of spinal process fusion plates. With that in mind, exemplary spinous process implants, according to the technology, may include a spacer and an extension extending outwardly from the spacer. The extension, which may be referred to as a wing, is sometimes described as being one or more lobes associated with the spacer. In certain aspects, the spacer may be integral or monolithic with one of the extensions. In other aspects, the spacer may be separate from all of the associated wings. The spinous process implant may be configured for insertion between adjacent spinous processes of the cervical, thoracic, and/or lumbar spine. The spacer may be provided in a variety of sizes to accommodate anatomical variation amongst patients and varying degrees of space correction. The spacer and extensions may include openings, recesses, pockets, etc. to facilitate tissue in-growth to anchor the spacer to the vertebral bodies such as tissue in-growth from the spinous processes. The spacer may be configured for tissue in-growth from superior and inferior spinous processes to cause fusion of the adjacent spinous processes. The openings may be relatively large and/or communicate to a hollow interior of the spacer or a hole, pocket, or recess in the extensions. A hollow interior may be configured to receive bone growth promoting substances such as by packing the substances into the hollow interior. The openings may be relatively small and/or comprise pores or interconnecting pores over at least a portion of the spacer surface. The openings, however formed, may be filled with bone growth promoting substances.

In certain aspects, the implant may be described as telescoping. A telescoping implant may generally be described as an implant that has multiple parts where at least a portion of the parts comprises a male protrusion that slidably engages a female socket to allow the male protrusion to slidably engage the female socket. A telescoping spinous process fusion plate may offer a number of functional advantages over other implants, such as a fixed length spinous process fusion plate. In certain embodiments, the telescoping spinous process fusion plate may provide: (1) compression of fixation devices extending from the extensions into one or more spinous processes, then manipulating the implant to compress or distract the interspinous space by providing a compact or enlarged configuration of the implant, (2) may compress or lordose when using a posterior interbody (transforaminal lumbar interbody fusion (TLIF) or posterior lumbar interbody fusion (PLIF) for example) to reduce the risk of expulsion from the fusion site, (3) distraction without (or without compressing) the fasteners extending from the extension to allow for functionality similar to an adjustable height extension stop, and (4) facilitate implantation by providing a compact insertion state and an enlarged or expanded distraction state.

A compact or reduced height insertion state may be particularly useful when the supraspinous ligament (SSL) is left intact as the compact or collapsed height of the telescoping implant may be approximately four (4) millimeters to about ten (10) millimeters. In certain aspects the collapsed height of the implant may be four (4), six (6), or eight (8) millimeters. However, if the SSL is sacrificed or removed, the implant may be fully assembled and inserted directly to the interspinous space using a posterior approach. Providing a compact height of 4-8 or 4-10 millimeters may provide for a smaller incision and surgical corridor. Moreover, the compact or reduced height of the implant (reduced as compared to the expanded or enlarged height) also may facilitate implantation when the posterior aspects of the spinous process are abutting or in close proximity, sometimes referred to as "kissing." Also, when the SSL is sacrificed, the telescoping implant may be a unitary unit with extensions attached to both sides of the spacer.

Whether unitary or modular, the extension may extend transversely from the spacer relative to a spacer longitudinal axis to maintain the spacer between adjacent spinous processes. The extension may be described as foldable, extendable, deployable or the like from a flat configuration to facilitate minimally invasive implantation to an extended position to facilitate fusion. A single extension may extend in one or more directions or multiple extensions may be provided that extend in multiple directions. One or more extensions may be adjustable longitudinally relative to one another and/or the spacer to allow the extensions to be positioned laterally relative to the spinous processes. A moveable extension may be provided that is moveable axially relative to the spacer and another extension. Alternatively, a plurality of moveable extensions may be provided. For example, the extensions may clamp against the sides of the spinous processes to immobilize the spinous processes relative to one another and promote fusion between the adjacent vertebrae. The extensions may include fasteners engageable with the spinous processes. The fasteners may include sutures, wires, pins, straps, clamps, spikes, screws, teeth, adhesives, and/or other suitable fasteners. The fasteners may be integrated into the extensions or they may be modular. Modular fasteners may be adjustable, replaceable, and/or removable to allow tailoring of the kind and quality of fixation from rigid fixation to no fixation. The spacer, extensions, and/or fasteners may advantageously be made of different materials. For example, the spacer and extensions may be made of a relatively softer material while the fasteners may be made of a relatively harder material. For example, the spacer and/or extension may be made of a polymer and/or other relatively soft material and the fastener may be made of a metal and/or other relatively hard material.

Insertion of spinous process implants may be facilitated by a set of instruments alternately engageable with one another to increase the interspinous space and engageable with a spinous process implant to help maneuver it between adjacent spinous processes as has been described in some of the related applications described above and incorporated by reference. Moreover, instruments for the present spinous process implant may facilitate percutaneous operation whether through a cannula, tube, or lumen. The instruments may include mechanisms to facilitate telescoping, unfolding, opening, or deploying portions of the implant including the extensions and spacer. The instruments may include a draw internal or external to the spacer to pull the extensions in a direction such that the extensions are pried apart by a wedge or ramp.

It has been found that presently available interspinous implants, such as the device explained with reference to FIGS. 1-9, are good at stabilizing a spinal segment to allow it to fuse. The interspinous implant could be implanted with less tissue trauma percutaneously or through a tube, cannula, or lumen if the spacer was provided in a compact state and expanded to a distraction state subsequent to the placement of the spacer between adjacent spinous processes. In certain embodiments, the implant, when in the compact state, fits within the space between adjacent spinous processes without abutting both processes and in some cases, may fit within the space without abutting either spinous process until the implant is partially expanded.

In other embodiments, the implant may slightly distract the spinous processes when in the compact state. Expanding the spacer to the distraction state may be subsequent to manual distraction of the vertebral bodies or may be in conjunction with expanding the spacer. Expanding the spacer may be accomplished by providing a spacer body with a superior and inferior portion that have internal surfaces that are ramped to cooperatively engage an internal body that is wedge shaped or ramped such that drawing the internal body laterally through an interspinous space may cause at least one of the superior and inferior portions to move apart in a distraction direction. In other embodiments, the spacer may be mounted on a post that telescopes into a bore such that the post may be expanded from the bore to cause expansion. In still other embodiments, the extensions may have a post and socket where the post and socket allow for ratcheted movement to telescope the spacer.

In certain embodiments, one or both of the extensions may be a foldable or collapsible extension to further compact the implant prior to placement. One or more of the extensions may have offset fasteners on the foldable extension and corresponding bores into which the fasteners may fit to allow a flat or nearly flat configuration of the folded wing for the most compact delivery possible. The foldable extensions may fold about an axle or be hinged to allow for movement. A draw, rod, or hook may be connected to the hinge or axle to pull the hinge or axle towards the spacer that causes the face or surface of the extension to run up against an edge that forces the folded extension to unfold. In some embodiments, internal rods and ramps may be used to force the folded extension to unfold or open.

For completeness, reference will now be made to FIGS. 1-9 describing an exemplary embodiment of a spinous process implant with a fixed and non-expandable spacer as well as at least one fixed or non-foldable extension. As will be explained further below, the spacer may be replaced with an expandable or telescoping spacer that is expandable before or after implantation from a compact or insertion state to a distraction or expanded state. While specific exemplary embodiments are provided herein, implants associated with any of the incorporated applications or similar spinous process fusion plates may benefit from the technology of the present application to allow telescoping or expanding implants with or without extensions or wings that fold to facilitate implantation. Moreover, it may be especially beneficial to incorporate a foldable extension with the technology of the present application to allow for a compact implant for delivery through minimally invasive procedures, for example.

Figure 2:
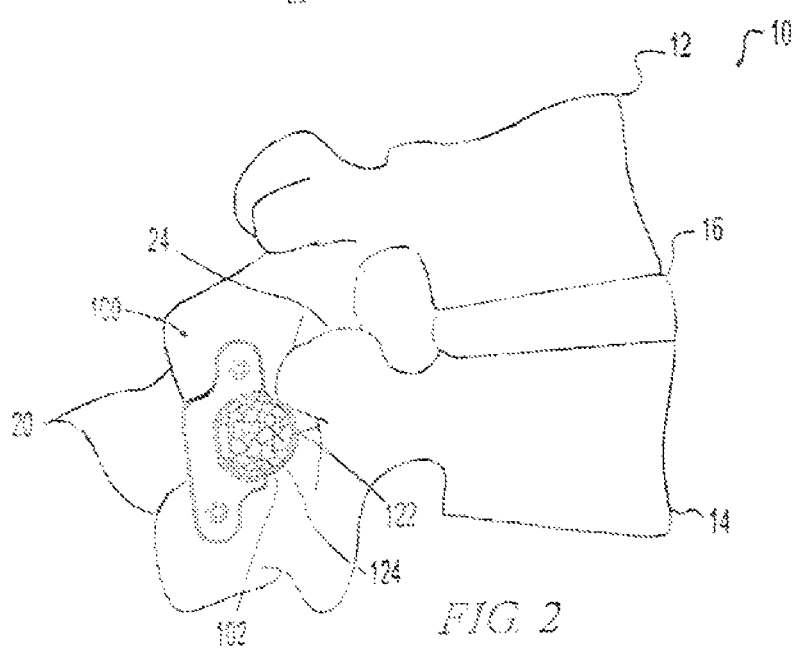
FIG. 2 is a side elevational view of the implant of FIG. 1 in situ.

FIGS. 1 and 2 depict posterior and lateral views of a pair of adjacent vertebrae of the lumbar spine 10. A superior vertebra 12 is separated from an inferior vertebra 14 by a disc 16. Each vertebra includes a pair of transverse processes 18, 19, a posteriorly projecting spinous process 20, 21, and a pair of lamina 22, 23 connecting the transverse processes 18, 19 to the spinous process 20, 21. In addition to the connection through the disc 16, the vertebrae 12, 14 articulate at a pair of facet joints 24.

FIGS. 1-9 illustrate an exemplary spinous process implant 100. The implant 100 includes a spacer 102 positioned between the spinous processes 20, 21. The geometry of the implant 100 is illustrated with the use of axes that define length (l), height (h), and width (w) directions for the spacer. When implant 100 is implanted in a patient, the height direction of the spacer 102 is generally oriented along the superior/inferior direction of the patient's anatomy, the width direction of the spacer 102 is generally oriented along the anterior/posterior direction of the patient's anatomy, and the length direction of the spacer 102 is generally oriented along the lateral/medial direction of the patient's anatomy.

The height 104 (FIG. 1) of spacer 102 limits how closely the spinous processes 20, 21 can move together. As the implant in this example is a fusion plate, the height also limits how distantly the spinous processes 20, 21 can move apart. Thus, the spacer 102 maintains a minimum and maximum distance between the spinous processes 20, 21. In the case of spine disease involving posterior subsidence of the adjacent vertebra, insertion of the spacer 102 between the spinous processes 20, 21 will move the vertebrae apart and relieve pressure on nerve tissue and the facet joints 24.

Figure 3:
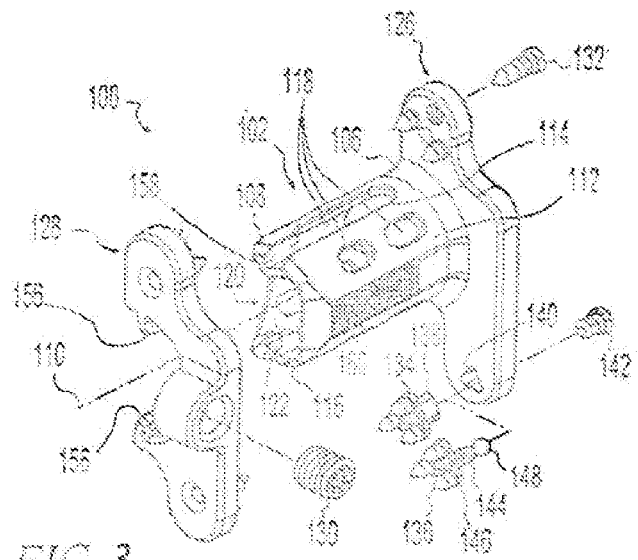
FIG. 3 is an exploded perspective view of the implant of FIG. 1.

As shown in FIG. 3, the spacer 102 includes a first end 106, a second end 108, and a longitudinal axis 110 extending from the first end to the second end. The spacer 102 has a sidewall 112, generally parallel to the longitudinal axis 110, including superior and inferior outer surfaces 114, 116. Transverse openings 118 (see also FIG. 6) communicate from the superior and inferior outer surfaces 114, 116 inwardly to facilitate tissue in-growth. The exemplary spacer 102 includes a hollow interior 120 bounded by an inner surface 122 such that the openings 118 communicate from the outer surfaces 114, 116 to the hollow interior 120. Bone growth promoting substances 124 are shown packed into the hollow interior 120 in FIGS. 1 and 2 to promote fusion of the vertebrae 12, 14 by bone growth between the spinous processes 20, 21.

The spinous process implant 100 further includes a first extension 126 projecting outwardly from the spacer 102 along the spacer height direction h and transversely to the longitudinal axis 110 to lie generally alongside the superior and inferior spinous processes 20, 21. Abutment of the first extension 126 with the spinous processes 20, 21 helps prevent lateral movement of spacer 102, thereby maintaining spacer 102 between the spinous processes 20, 21. In the exemplary spinous process implant 100, the first extension 126 is fixed relative to the spacer 102. When fixed, the first extension 126 may be generally unitary with spacer 102 or the first extension 126 and spacer 102 may form a monolithic unit. The implant 100 also includes a second extension 128 mountable to the spacer for axial movement relative to the first extension 126. The second extension 128 may be moved toward the first extension 126 to approximate the width of the spinous processes 20, 21 and better stabilize the implant 100. It is fixed in place by tightening a set screw 130 (FIG. 3) against the spacer 102. The extensions 126, 128 include fasteners 132, 134, 136 projecting from the extensions 126, 128 to engage the spinous processes 20, 21 to fix the spacer 102 to the spinous processes 20, 21. FIG. 1 depicts an additional bone growth promoting substance in the form of strips of bone 125 sandwiched between the extensions 126, 128 along the sides of the spinous processes 20, 21 to promote bone growth along the sides of the spinous processes to further enhance fusion of the vertebrae 12, 14. As an alternative to strips of bone 125, the bone 125 may be formed similar to a washer or ring to cooperatively fit about the fasteners 132, 134, 136 to promote bone growth. While the extensions 126, 128 may extend in only one of inferiorly or superiorly from the spacer 102, the extensions 126, 128 preferably extend inferiorly as well as superiorly from spacer 102 to optionally attach to both the inferior and superior spinous processes to immobilize the spinous processes 20, 21 relative to one another while fusion takes place.

Fasteners 132, 134, and 136 may take any suitable form. They may be made integral with the extensions 126, 128 such as by machining or casting them with the extensions or they may be formed separately and permanently attached to the extensions 126, 128. Fastener 132 is a sharpened spike that threadably engages the extension 126. The threaded engagement allows the fastener 132 to be replaced with a different fastener 132. For example, the fastener 132 may be replaced by one that has a different shape, a different size, a different material, or a different surface coating. The threaded engagement also allows the fastener 132 to be adjusted to extend by varying amounts from the extension 126 to vary how it engages the bone. Thus, the fastener 132 can be adjusted to fit differently shaped bones or to penetrate into a bone by varying amounts. For example, multiple threaded fasteners 132 can be adjusted to extend by different amounts to conform to curved or angled bone. Finally, the threaded engagement allows the user to remove the fastener 132 when fixation is not desired such as when it is desired to use implant 100 in a non-fusion procedure as an extension stop without limiting flexion.

As best seen in FIG. 3, fasteners 134 and 136 are provided as multi-spike pods allowing a plurality of spikes to be quickly adjusted, changed, or omitted. Fastener 134 includes a non-circular tab 138 engageable with a non-circular opening 140 in the extension 126. The non-circular engagement prevents the fastener 134 from rotating. The tab 138 may form a press-fit, snap-fit, or other suitable engagement with the opening 140. The tab 138 may be further secured by a supplemental screw 142. Fastener 136 includes a threaded shaft 144 threadably engaged with a base member 146 to allow the length of the fastener 136 to be adjusted. The shaft 144 engages the extension 126 in a rotating and pivoting manner such that the fastener 136 can be adjusted rotationally and angularly to engage the bone surface. In the illustrative embodiment, the shaft 144 terminates in a spherical ball 148 that engages the opening 140 in a ball-and-socket arrangement for three degrees of freedom. However, any mechanism that allows any number of degrees of freedom may be used. The fastener 136 may be allowed to move in use so that as the extension 126 is pressed toward a bone, the fastener 136 adjusts to the angle of the bone surface. The fastener 136 also may be secured, such as by screw 142, to adjust the tension in the joint and/or to lock the fastener 136 in a predetermined orientation.

Figure 4:
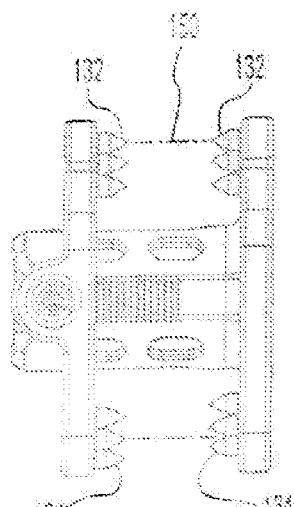
FIG. 4 is a posterior elevational view of the implant of FIG. 1.

FIG. 4 illustrates the axial relationship of fasteners on the opposing extensions 126, 128. In the illustrative implant 100, the fasteners 132 at the top of the implant 100 are shown aligned along a common axis 150 that is substantially perpendicular to extensions 126 and 128. The fasteners 134 at the bottom of the implant 100 are shown offset so that they can interleave, if necessary, as they are pressed into a bone. Any combination of fastener type, number, and alignment may be provided on the implant 100.

Figure 5:
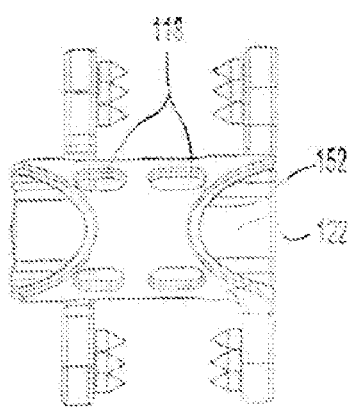
FIG. 5 is an anterior elevational view of the implant of FIG. 1.
Figure 6:
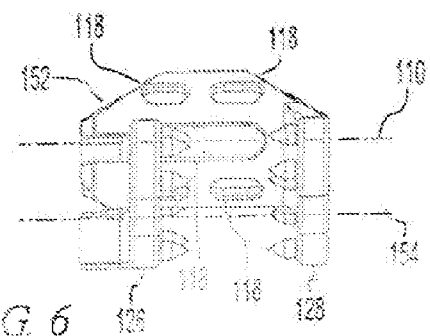
FIG. 6 is a top plan view of the implant of FIG. 1.

As seen in FIGS. 5 and 6, the ends 106, 108 of the spacer 102 include anterior chamfers 152. These chamfers 152 allow the ends 106, 108 to clear posteriorly facing structures of the vertebrae 12, 14 such as the facet joints 24. Also, as seen in FIGS. 5 and 6, the spacer 102 is offset anteriorly (in the spacer width direction w) relative to the extensions 126, 128 such that the longitudinal axis 110 of the spacer 102 is anterior of a midline plane 154 (FIGS. 6, 8) of the extensions 126, 128. The anterior offset of the spacer 102 allows it to fit deeply between the spinous processes 20, 21 while the extensions 126, 128 fit alongside the spinous processes 20, 21.

Figure 7:
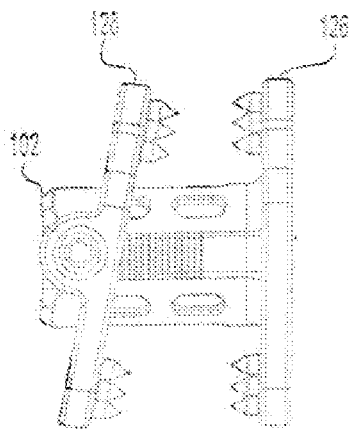
FIG. 7 is a posterior elevational view of the implant of FIG. 1 showing the assembly in an alternate position.
Figure 8:
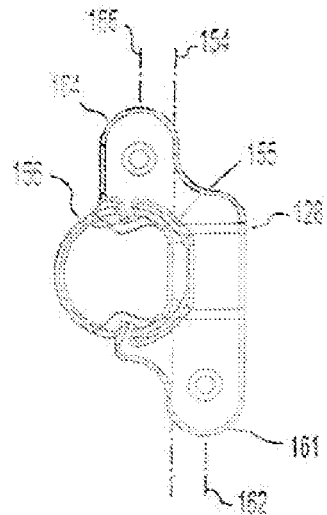
FIG. 8 is a side elevational view of the implant of FIG. 1.

As best seen in FIGS. 3 and 8, the second extension 128 defines an aperture 155 conforming generally to the cross-sectional shape of the spacer 102. In the illustrative embodiment of FIGS. 1-9, the aperture 155 opens anteriorly to form a "C"-shape, although the aperture 155 could conform to the entire cross-section of the spacer to form a "D" or "O" shape, for example. In the exemplary embodiment, aperture 155 forming a generally "C"-shape includes tabs 156 that extend inwardly from the superior and inferior portions of the aperture to slidingly engage elongated slots 158 in the superior and inferior surfaces of the spacer 102. The second extension 128 can be translated longitudinally along the spacer length l toward and away from the first extension 126. Tightening the set screw 130 against the posterior side 160 of the spacer 102 forces the tabs 156 posteriorly against the sides of the slots 158 and locks the second extension 128 in place longitudinally. The tabs 156 may increase towards the tip of the tabs 156 to facilitate engagement with the slots 158 in the spacer 102. The tabs 156 may be hooked shaped as well instead of straight or expanding to facilitate the cooperative engagement. The posterior side 160 of the spacer 102 may be roughened as shown to better grip the set screw 130. The set screw 130 may also dig into the surface of the spacer 102 upon tightening to positively grip the spacer 102. The aperture 155 (FIGS. 3, 8) may conform closely to the spacer 102 to constrain the second extension 128 to generally parallel motion relative to the first extension 126. Alternatively, the aperture 155 may be larger than the spacer 102 by a predetermined amount to permit a predetermined amount of angular adjustment of the second extension 128 relative to the first extension 126 as shown in FIG. 7 to allow the extension 128 to adjust to the underlying bone surface.

Figure 9:
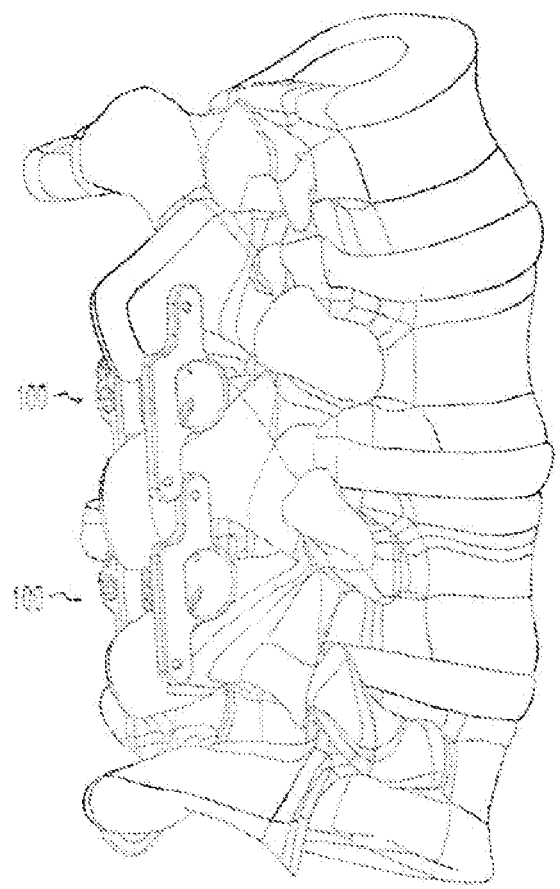
FIG. 9 is a perspective view of a pair of implants like that of FIG. 1 in situ.

As best seen in FIG. 8, the second extension 128 includes a first inferior lobe 161 having a first lobe centerline 162 and a second superior lobe 164 having a second lobe centerline 166. In the illustrative embodiment, the first lobe centerline 162 and the second lobe centerline 166 are parallel and spaced apart so that the second extension 128 has a generally "Z"-shaped plan form. This shape allows the extension of one implant 100 to interleave, if necessary, with another implant 100 in a multilevel surgery (as shown in FIG. 9) to permit close spacing of the implants, and/or longer extension lobes for more extensive bone engagement. In addition, first inferior lobe 161 has a semi-circular convex shape that is generally complementary to a semi-circular superior concave surface 165 formed adjacent second superior lobe 164. Similarly, second superior lobe 164 has a semi-circular convex shape that is generally complementary in shape to a semi-circular inferior concave surface 163 formed adjacent first inferior lobe 161. As indicated in FIG. 8, first inferior lobe 161 is adjacent to inferior concave surface 163, and extension midline plane 154 is located between first inferior lobe 161 and inferior concave surface 163. Second superior lobe 164 is adjacent superior concave surface 165, and extension midline plane 154 is located between second superior lobe 164 and superior concave surface 165. Moreover, first inferior lobe radius $r_1$ is substantially equal to superior concave surface radius $r_4$, while second superior lobe radius $r_3$ is substantially equal to inferior concave surface radius $r_2$. As a result, when two implants are placed on adjacent spinal levels, the first inferior lobe 161 of the upper implant may be (but need not be, depending on what is medically indicated) interfitted into the superior concave surface 165 of the inferior implant. In addition, the second superior lobe 164 of the inferior implant may be interfitted into the inferior concave surface 163 of the superior implant. In the illustrative example of FIGS. 1-9, first inferior lobe 161 and second superior lobe 164 form a unitary second extension 128. Although not separately depicted, first extension 126 also has complementary lobes that are similarly configured and oriented relative to one another.

As shown in FIG. 9, multiple spinous process implants 100 may be placed on adjacent levels of the spine. As illustrated in the figure, a first superior implant 100 is positioned with its spacer 102 between a first superior spinous process and a second intermediate spinous process, while a second inferior implant 100 is positioned with its spacer 102 between the second intermediate spinous process and a third inferior spinous process. The first extensions 126 of the superior and inferior implants are located on a first side of the patient's sagittal plane, while the second extensions 128 of the superior and inferior implants are located on a second side of the patient's sagittal plane.

In the illustrative embodiment of FIGS. 1-9, the extension lobe centerlines 162,166 are offset equidistantly from the midline plane 154 of the second extension 128. Although not separately shown, the first extension 126 is configured similarly. The centerlines 162, 166 may vary from parallel and they may be offset asymmetrically to form different shapes to accommodate different vertebral anatomy. For example, the shape may be tailored for different portions of the spine 10. In the illustrative embodiment of FIGS. 1-9, the first extension 126 has the same shape as the second extension 128. However, the shape may be varied between the first and second extensions 126, 128.

As shown in FIGS. 1-9, the first extension 126 is integral or unitary with the spacer 102 and second extension 128 has an aperture 155 that is shown to partially surround the spacer to allow the second extension 128 to translate over the outer surface of the spacer 102. In certain embodiments, especially smaller implants, the aperture 155 may form a through hole in second extension 128 to completely surround the spacer 102.

Figure 10A:
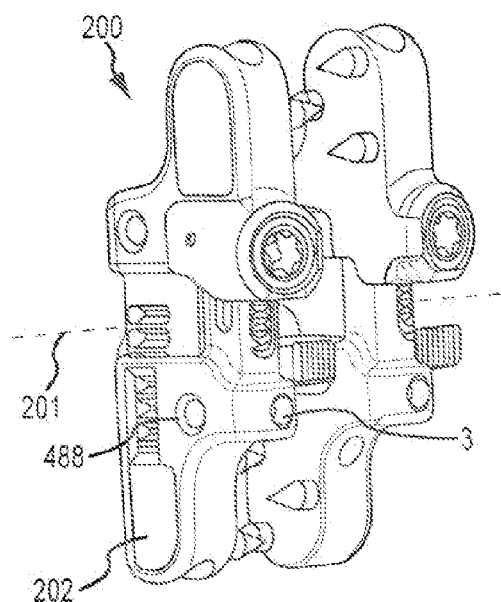
FIGS. 10A-D are views of an implant that is consistent with the technology of the present application.
Figure 10B:
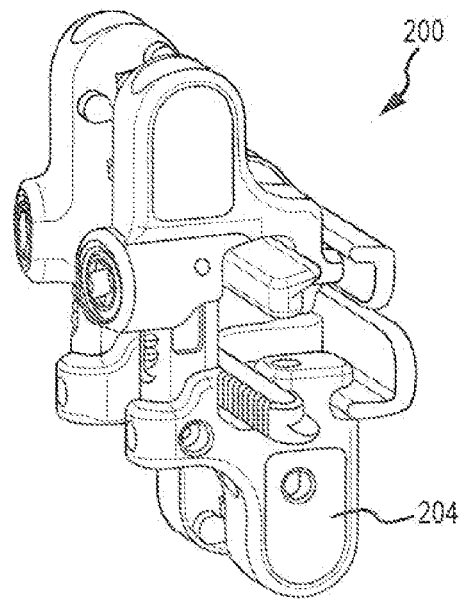
Figure 10C:
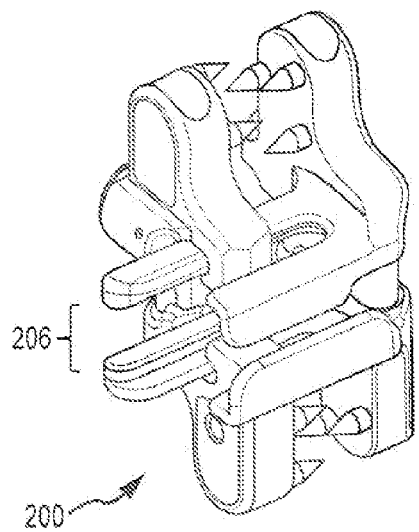
Figure 10D:
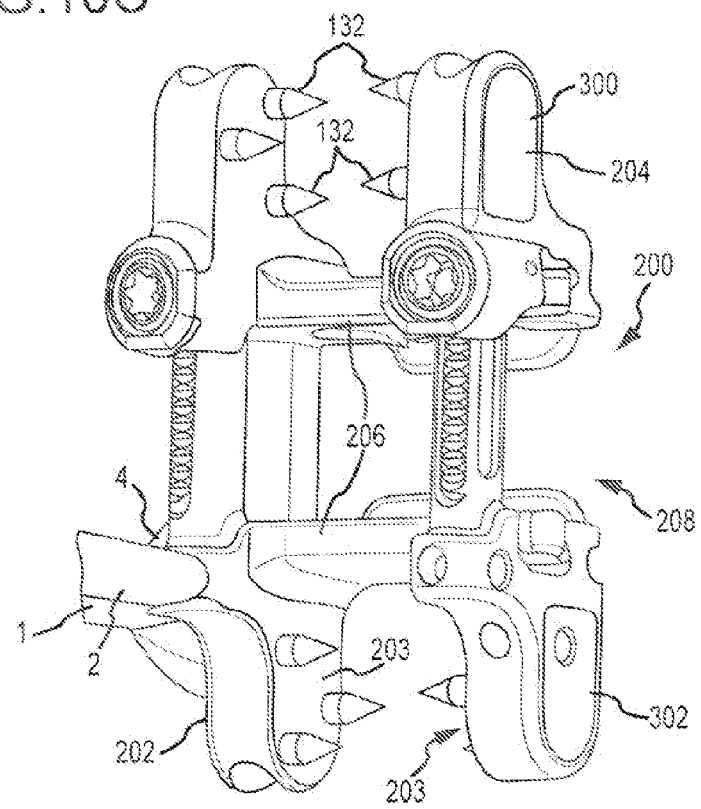

Now, with reference to the remaining FIGS., an implant 200 is described. The implant 200 is shown in FIGS. 10A, 10B, and 10C in a posterior/left lateral view (10A), a right lateral/posterior view (10B), and an anterior/right lateral view (10C) in a partially expanded state. In other words, the implant 200 is not shown completely compacted or completely expanded. As shown, the implant 200 includes a first extension or wing 202 and a second extension or wing 204. The first extension 202 may be referred to as the post plate because a plurality of arms 206 (which will be explained further below) may be monolithic with the first extension 202. In the embodiment shown in FIGS. 10A-10D, the plurality of arms 206 are cantilevered from the first extension or post plate 202 along a horizontal or transverse axis 201. The second extension 204 may be referred to as the lock plate because it is generally free to move with respect to the plurality of arms 206 until it is locked in place (as will be explained further below). FIG. 10D shows implant 200 in a fully or close to fully extended or distracted state 208. As can be appreciated, the spacer 102 of implant 100 has been replaced by four (4) arms 206 extending from first extension 202. One of ordinary skill in the art on reading the disclosure, however, would now understand that the plurality of arms 206 is only one exemplary embodiment of the present technology and the plurality of arms 206 may be replaced by more, less, or differently configured members that function as the spacer.

As shown in FIGS. 10A-D, the first and second extensions 202, 204 have medial sides 203 with fasteners, such as fasteners 132 described above. The fasteners on the medial sides 203 may include any of the fasteners described above or in any of the incorporated applications.

Figure 11:
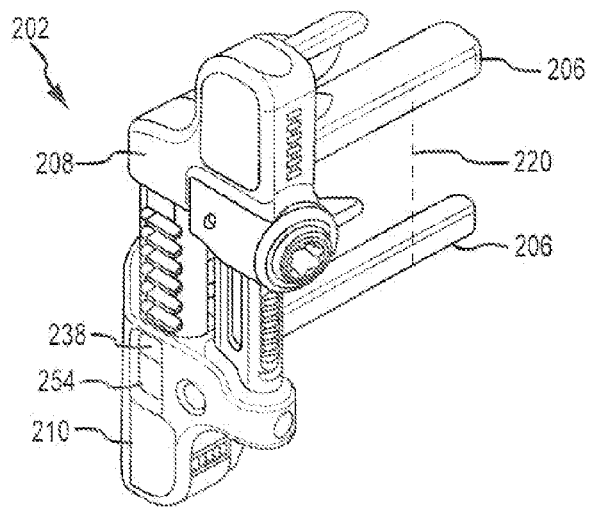
FIG. 11 is a perspective view of a part of the implant.
Figure 12:
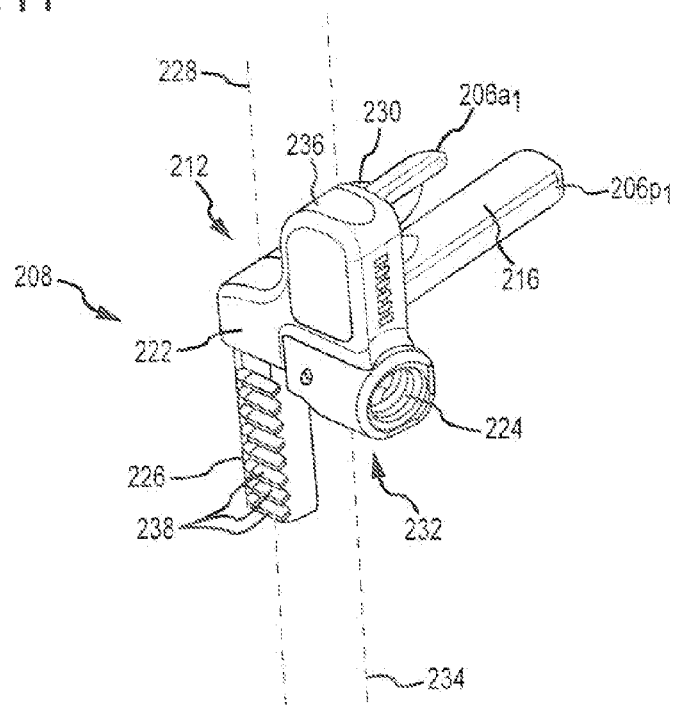
FIG. 12 is a perspective view of a part of the implant.
Figure 13:
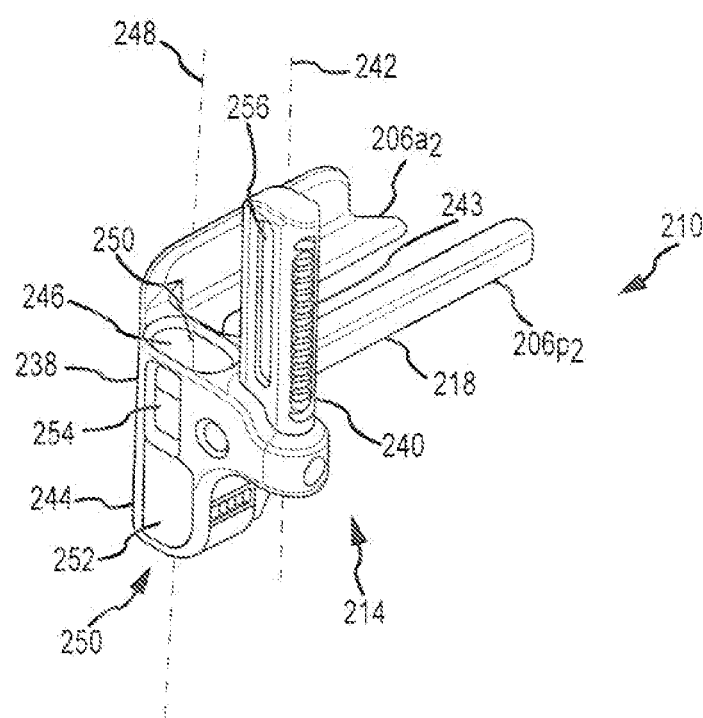
FIG. 13 is a perspective view of a part of the implant.

With reference to FIGS. 11-13, the first extension 202 and the plurality of arms 206 of implant 200 are shown. The first extension 202 includes a first part 208 (FIG. 12) and a second part 210 (FIG. 13). The first and second parts 208, 210 have an anterior facing side 212 and a posterior facing side 214. The first and second parts 208, 210 further include an anterior arm $206a_1$ and $206a_2$ and a posterior arm $206p_1$ and $206p_2$. While shown as two anterior arms and posterior arms, the plurality of arms 206 may include more or less arms. For example, anterior arm $206a_1$ may be formed contiguous with posterior arm $206p_1$. Alternatively, there could be more arms, such as an anterior arm, a posterior arm, and an interior arm. The arms $206a_1$ and $206p_1$ of the first part 208 have a top surface 216. The arms $206a_2$ and $206p_2$ of the second part 210 have a bottom surface 218. A distance 220 between the top surface 216 and the bottom surface 218 is adjustable, as will be explained below, from a minimum to a maximum distance.

As seen in FIG. 12, the first part 208 has a central portion 222 that extends from the anterior facing side 212 to the posterior facing side 214. As used herein, central portion should not be construed to mean a middle, midline, or other geometric reference. Rather the phrase central portion is a designator that the portion is in between, for example, inferior and superior extending parts as will be explained further below. A threaded bore 224 opens towards the posterior facing side 214. As will be explained further below, a set screw or the like is threadably engaged with the threaded bore 224 to lock the first part 208 at a height when the distance 220 is the desired spacing between the superior and inferior spinous processes.

Extending in an inferior direction from the central portion 222 is a male member 226. The male member 226 is on the anterior side of the first part 208. The male member 226 has a vertical axis 228. Extending in a superior direction from the central portion 222 is a female member 230. The female member 230 generally conforms to, for example, the lobes addressed above with respect to FIGS. 1-9. In other words, the female member 230 generally conforms to a superior lobe described above. The female member 230 is generally hollow and forms a socket 232. The female member also has a vertical axis 234 offset in a posterior direction from the vertical axis 228. The female member 230 has an opening 236 at both ends of the socket 232 to reduce the material and overall profile of the implant. The top opening 236 could be closed with a web of material. However, the female member 230 would need to extend to a greater height along the vertical axis 234 to accommodate a similar sized male member.

The male member 226 has a plurality of indentations 238, rack cutouts, ratchets, gears, or teeth. A tool, not shown in FIGS. 11-13, has a plurality of corresponding protrusions to engage the teeth. Rotating the protrusions on the tool acts as a pinion gear and causes the male member 226 to move up or down along the vertical axis 228. With reference to FIG. 10D, a tool 1 is shown attached to the first extension 202. The tool may have an arm 2 that terminates in a protrusion (not shown) that engages a detent or hole 3 on the first extension 202. A pinion gear may be contained in a housing 4 to engage the indentations. The pinion gear may be rotated by a dial (not shown) connected to a handle distal to the housing 4 using, for example, a worm drive or the like.

As seen in FIG. 13, the second part 210 has a central portion 238 that extends from the anterior facing side 212 to the posterior facing side 214. Extending in a superior direction from the central portion 238 is a male member 240. The male member 240 is on the posterior side of the second part 210. The male member 240 has a vertical axis 242 that is substantially aligned with vertical axis 234 of the female member 230 on the first part 208. The male member 240 is sized for telescopic movement in and out of the socket 232. The male member 240 may have surface texturing 243 in a posterior face to engage a set screw, or the like, threaded into threaded bore 224 (above). Extending in an inferior direction from the central portion 238 is a female member 244. The female member 244 generally conforms to the inferior lobes described above with respect to FIGS. 1-9. The female member 244 is generally hollow and forms a socket 246. The female member also has a vertical axis 248 that is substantially aligned with the vertical axis 228 of the male member 226 of the first part 208. The socket 246 is sized to allow telescopic movement of male member 226 in and out of the socket 246. The socket 246 forms a through bore in the female member such that has openings 250 on the top and bottom, although the bottom opening 250 may be closed with a web of material.

A lateral side 252 of the female member 244 has an opening or window 254. The indentations 238 of the male member 226 are visible through the window 254. The tool, explained above but not shown in FIGS. 11-13, has protrusions that extend through the window 254 to engage the indentations.

FIGS. 14-17 show implant 200 in a compact state 260. FIG. 13 shows a view along the horizontal axis 201 of the lateral side 252 of the first extension 202. The first part 208 and the second part 210 are shown abutting along an edge 262. The first and second part 208, 210 do not need to abut along the edge 262, but allowing the first and second parts 208, 210 to abut provides a low profile. Prior to implantation, the implant 200 may be held assembled in the compact state 260 using a pin 264 in a pin hole 266 where the pin 264 extends through the female member 230 of the first part 208 and engages the male member 240 of the second part 210, such as, for example, by engaging a groove 256. Alternatively, set screw 268 could be threaded into threaded bore 224 to hold the parts together.

The female members 230, 244 are shown extending in the superior and inferior direction, respectively. The male member 222 is shown fully inserted into socket 246 and visible through window 254. The male member 240 is fully inserted into socket 232, but not visible in the lateral view.

Figure 15:
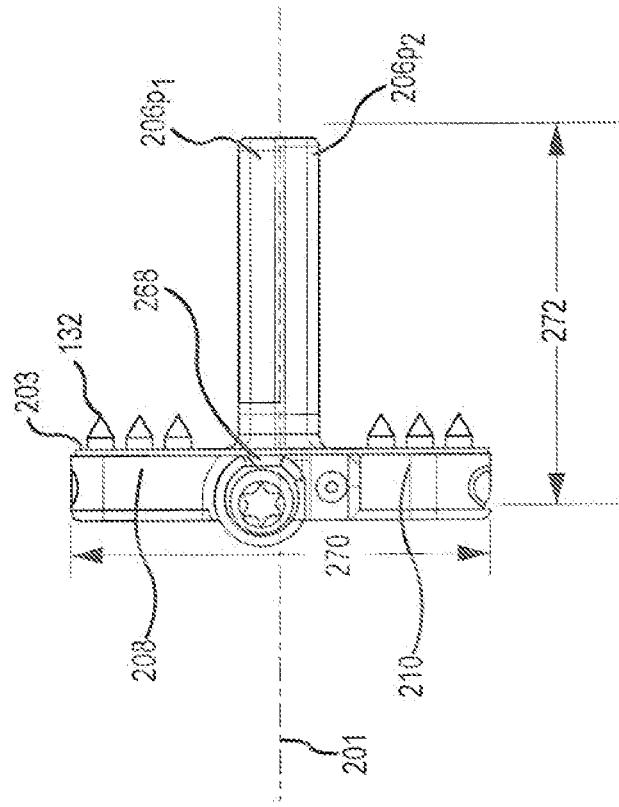
FIG. 15 is a view of a part of the implant.
Figure 14:
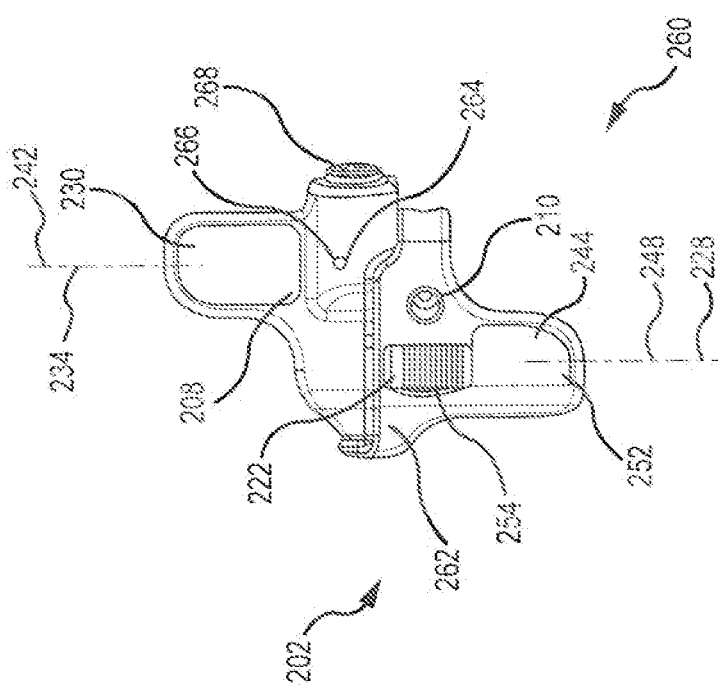
FIG. 14 is a view of a part of the implant.

FIG. 15 shows the first extension 202 from a posterior view in the compact state 260. In the compact state 260, the first extension 202 has a height 270. The posterior arms $206p_1$ and $206p_2$ abut in the compact state 260 to provide a low profile in the compact state (in other words, the height 270 is as small as possible), although they could be slightly separated. The first extension 202, including the plurality of arms, extends in the horizontal direction a length 272.

FIG. 16 shows the first extension 202 from a medial view in the compact state 260. In the compact state 260, the anterior arms $206a_1$ and $206a_2$ nest such that anterior wall members 276, 277 are in a sliding relationship when in the compact state. The anterior wall members may be referred to herein as vertical wall members, anterior flaps, or the like. The posterior arms $206p_1$ and $206p_2$ abut, but could be designed to nest similar to the anterior arms $206a_1$ and $206a_2$. As shown, each of the arms for a vertical wall and an overhang 278 forming a quasi chamber 280 into which bone growth may occur. Additionally, bone growth promoting substances may be contained in the chamber 280.

Figure 18:
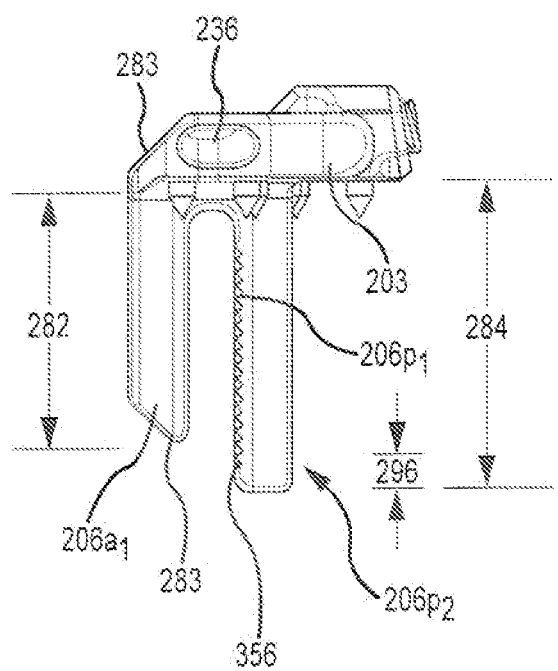
FIG. 18 is a view of a part of the implant.

FIG. 17 shows the first extension 202 from an anterior view in the compact state 260. As can be appreciated with respect to FIGS. 17 and 18, where FIG. 18 shows a superior view of the first extension, the anterior arms $206a_1$ and $206a_2$ extend from the medial side 203 a length 282. The anterior arms may terminate in a chamfered terminal end 283 to facilitate implantation of the implant 200. Similarly, the posterior arms $206p_1$ and $206p_2$ extend from the medial side 203 a length 284. As shown, the length 284 of the posterior arms is longer than the length of the anterior arms 282 by a distance represented by 286. The shorter anterior arms facilitate clearing portions of the anatomy, such as the facet, during certain implantation procedures.

Figure 19:
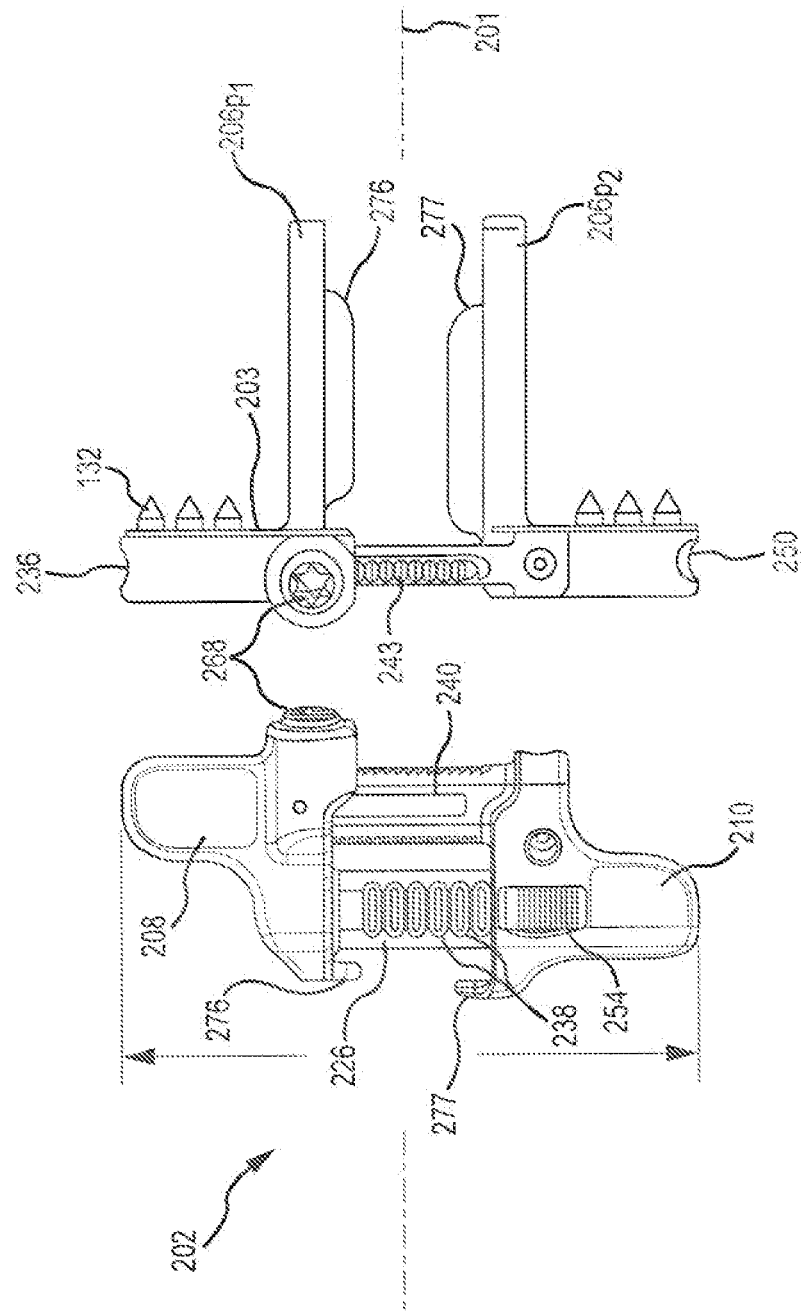
FIG. 19 is a view of part of the implant.

FIG. 19 shows the first extension 202 in the fully extended state 288 in both a lateral and posterior view. The first extension 202 in the extended state 288 has a maximum height 290 greater than the height 270 in the compact state. The extended state 288 may be referred to as the distracted or distraction state. As can be appreciated, the first extension 202 may be moved from the compact state 260 to an extended state where the height is less than the maximum height 290 shown in FIG. 19. The set screw 268 engaging the texture 243 holds the first part 208 and the second part 210 in position once the position is set by the surgeon.

The first extension 202 provides dual male-female telescoping members as described above. The dual telescoping members allow for the plate to substantially change height while maintaining a sufficient aspect ratio to reduce frictional binding during actuation and also to increase rigidity of the final construct. In some embodiments, the male-female telescoping pairs are arranged so that the female member of each telescoping feature is positioned offset so that the male member of each telescoping feature fully resides inside the member, with no protrusions in the compact state. Such an arrangement prevents or helps prevent interference when nesting additional plates at the adjacent levels for multilevel use. In some embodiments, two implants are used to connect across or collectively span two adjacent interspinous spaces. In other embodiments, three or more implants are used to connect across three or more interspinous spaces. Additionally, it can be appreciated now that the male members and the female members may be reversed and the above description including lateral, medial, superior, inferior, anterior, and posterior directions or guides is to facilitate identification of different pieces and parts of the device and should not be considered limiting.

Figure 20:
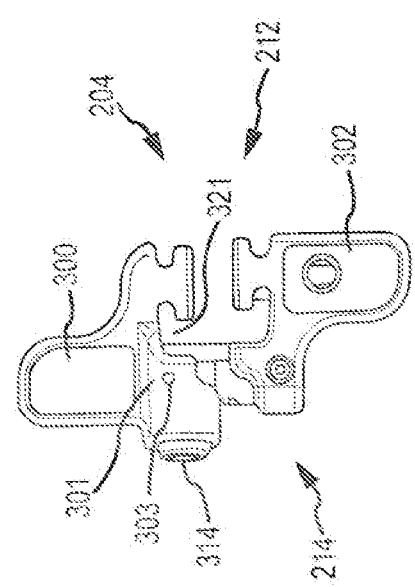
FIG. 20 is a view of part of the implant.

With reference back to FIGS. 10A-D, the second extension 204, which is sometimes referred to as the lock plate, comprises a third part 300 and a fourth part 302, both of which are shown in a lateral view along horizontal axis 201 in FIG. 20. The third part 300 and fourth part 302 similar to the first part 202 and second part 204 have an anterior facing side 212 and a posterior facing side 214. As shown, third part 300 includes a pin hole 301 that receives a pin 303. As will be explained below, the pin 303 extends through pin hole 301 and loosely couples the third part 300 and the fourth part 302.

Figure 21:
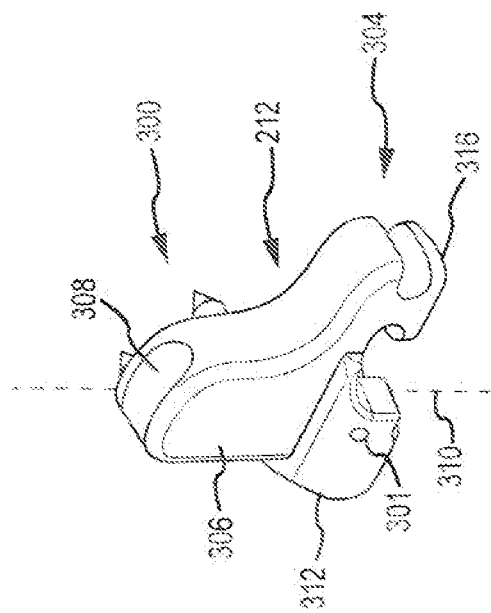
FIG. 21 is a perspective view of a part of the implant.

FIG. 21 shows an anterior, lateral perspective view of the third part 300. The third part 300 includes a central portion 304 with a posterior, female member 306 extending in a superior direction from the central portion 304. The female member 306 generally conforms to a superior lobe of the section extension described above with respect to FIGS. 1-9. The female member 306 is generally hollow forming socket 308 and has a vertical axis 310. The central portion 304 of the third part 300 includes a threaded bore 312 that receives a set screw 314 to lock the third part 300 to the fourth part 302, as will be explained further below.

Figure 22:
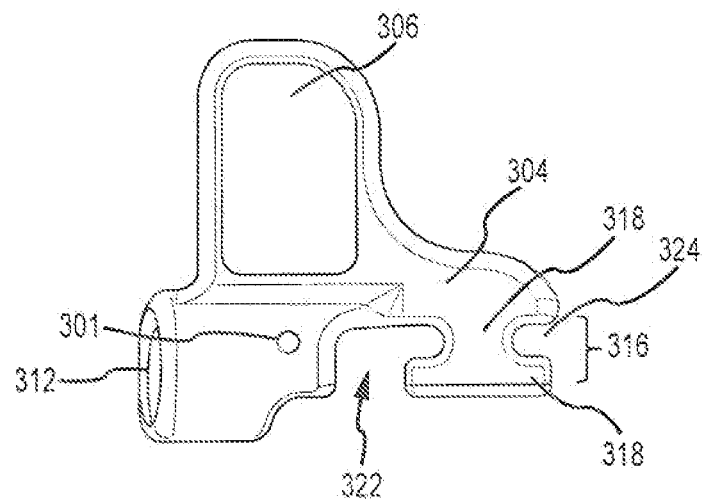
FIG. 22 is a view of a part of the implant.

An anchor 316 or truncated male member extends in an inferior direction from the central portion 304. As shown in FIG. 22, the anchor 316 has a short post 318 that terminates in a flanged surface 320. The central portion 304, post 318, and flanged surface 320 form a first interior cavity 322. With reference back to FIG. 16, for example, the first cavity 322 is shaped to cooperatively, and slidingly, engage the posterior arm $206p_1$, which includes the overhang 278. Similarly, the central portion 304, post 318, and flanged surface 320 form a first exterior cavity 324, which may be sometimes referred to as a carve out or groove. The first exterior cavity 324 is shaped to cooperatively, and slidingly, engage the overhang 278 of the anterior arm $206a_1$. As can be appreciated, the more snugly the cavities 322 and 324 fit the arms $206p_1$ and $206a_1$, the less movement is provided. Increasing the size of the cavities may provide the ability to orient the third part 300 with respect to the patient anatomy. In the embodiment shown, the cavities are provided with an angled or chamfered surface 321 that provides the ability to adjust the angle of the third part in the coronal plane. The angle may be from about 0° degrees to about 10 or in some cases 15°.

Figure 23:
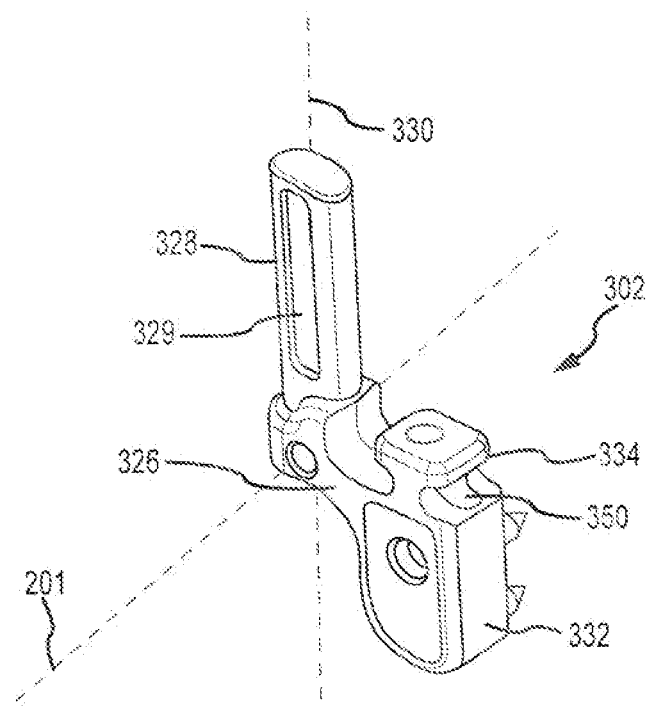
FIG. 23 is a perspective view of a part of the implant.

With reference now to FIG. 23, a view of the fourth part 302 is shown. The fourth part comprises a central portion 326. A posterior, male member 328 extends in a superior direction posterior facing side of the central portion 326. The male member 328 extends along a vertical axis 330. The vertical axis 330 of the male member 328 generally aligns with the vertical axis 310 of the socket 308 or female member 306. The male member 328 is sized for telescopic movement in and out of the socket 308. The male member 328 may include a channel. An anterior member 332 extends in an inferior direction from the central portion.

Figure 24:
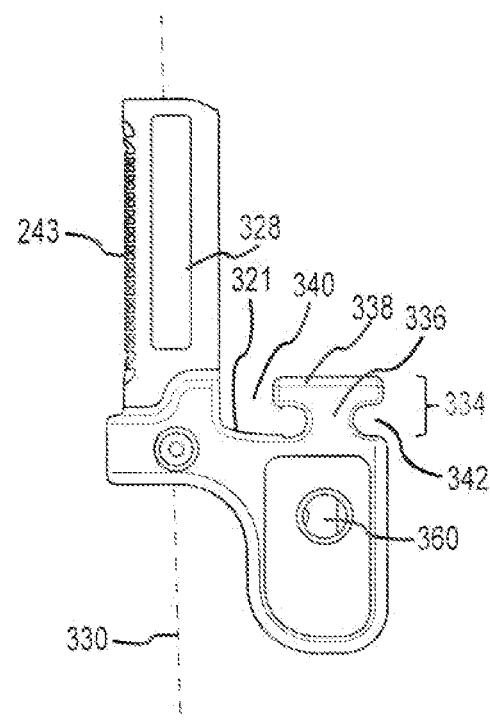
FIG. 24 is a view of a part of the implant.
Figure 26:
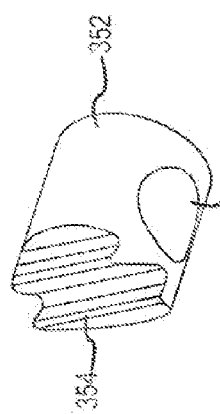
FIGS. 25-27 are views of parts of the implant consistent with the technology of the application.

An anchor 334, generally corresponding in size, form, and function to the anchor 316 above, extends in a superior direction from the central portion 326 as best seen in FIG. 24. The anchor 334 includes a short post 336 that terminates in a flanged surface 338. The central portion 326, post 336, and flanged surface 338 form a second interior cavity 340. With reference back to FIG. 16, for example, the second cavity 340 is shaped to cooperatively, and slidingly, engage the posterior arm $206p_2$, which includes the overhang 278. Similarly, the central portion 326, post 336, and flanged surface 338 form a second exterior cavity 342, which may be sometimes referred to as a carve out or groove. The second exterior cavity 342 is shaped to cooperatively, and slidingly, engage the overhang 278 of the anterior arm $206a_2$. As can be appreciated, the more snugly the cavities 340 and 342 fit the arms $206p_2$ and $206a_2$, the less movement is provided. Increasing the size of the cavities, may provide the ability to orient the fourth part 302 with respect to the patient anatomy. Similar to the cavities above, the cavities are provided with an angled or chamfered surface 321 that provides the ability to adjust the angle of the third part in the coronal plane. The angle may be from about 0° degrees to about 10 or in some cases 15°. Notice, the anterior arms and the posterior arms are each similarly shaped such that the first and second internal cavities, and the first and second external cavities, all have generally the same shape.

The posterior face 344 of the male member 328 includes surface texturing 243 similar to the posterior face of male member 240 described above. Thus, when the male member 328 is telescoped in female socket 308 to a desired position, the set screw 314 may be threaded in threaded bore 312 until the set screw engages the surface texturing 243 to secure the third part 300 with respect to the fourth part 302.

Figure 27:
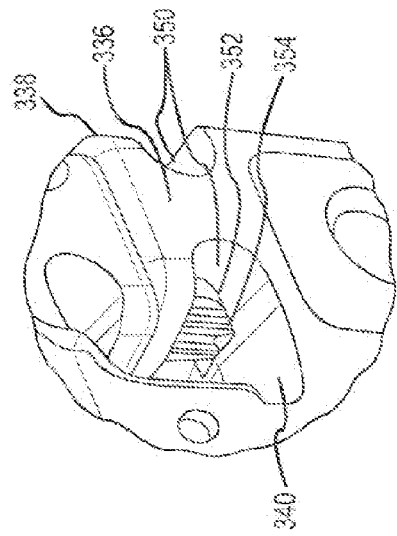
Figure 25:
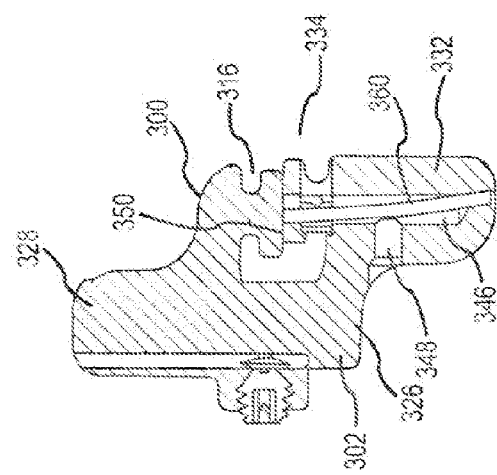

The anterior member 332, while hollow, does not form a socket similar to the other members described herein; in part, because third part 300 has an anchor 316 rather than a male member extending from the third part 300 in an inferior direction. Also, anterior member 332, which is shown in cross-section in FIG. 25, provides a means for coupling the second extension 204 to the plurality of arms 206, and more specifically, to the posterior arm $206p_2$ in this exemplary embodiment. As shown, anterior member 332 provides an elongate chamber 346 that has a posteriorly extending tool port 348 arranged in this embodiment below central portion 326. The elongate chamber 346 extends from the bottom of anterior member 332 to the flanged surface 338. The short post 336 has a posterior port 350 which is shown extending completely through short post 336 of anchor 334, but is only needed to extend from the elongate chamber 346 to the second internal cavity 340. A plunger 352 resides in the posterior port 350. The plunger 352 couples to the posterior arm $206p_2$ to hold the second extension 204 in place during the surgical procedure. In this exemplary embodiment, the plunger 352 may be considered a ratcheted plunger as the plunger 352 has a plurality of teeth 354 that engage corresponding teeth 356 (FIG. 18) on the posterior arm $206p_2$. The plunger is coupled to a spring arm 360, such as, by the spring arm 360 extending into a bore 358. The spring arm 360 biases the plunger in a posterior direction such that the plunger extends from the posterior port 350 to engage the posterior arm $206p_2$. As can be appreciated, the teeth are shaped to allow movement of the second extension toward the first extension without disengaging the plunger 352. However, to move the second extension away from the first extension, a tool needs to extend into tool port 348 to engage spring arm 360. The tool would move spring arm 360 in an anterior direction to allow the plunger 352 to disengage such that the second extension may be moved away from the first extension. FIG. 27 shows a view of the teeth 354 of the plunger 352 extending through posterior port 350 into the second internal cavity 340.

Figure 28:
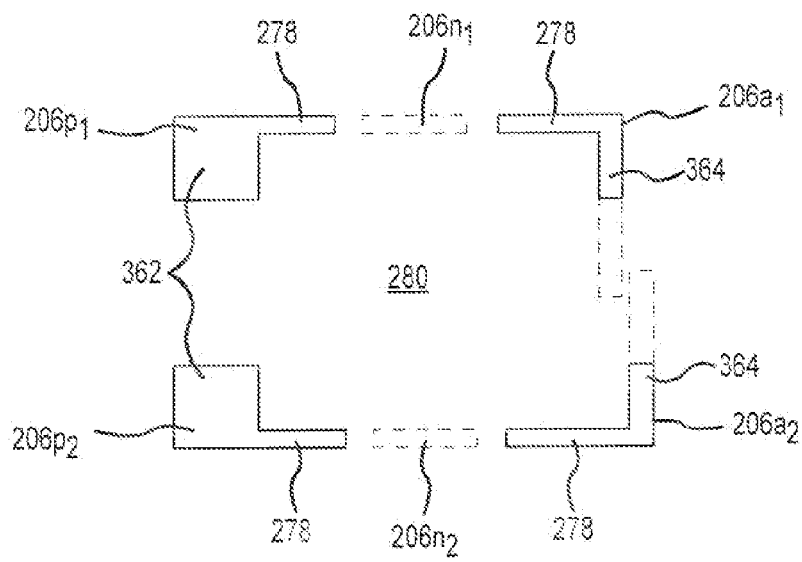
FIGS. 28-30 are views of parts of the implant consistent with the technology of the application.

FIG. 28 shows a cross sectional view of the plurality of arms 206 including the anterior arms $206a_1$ and $206a_2$, and the posterior arms $206p_1$ and $206p_2$. Each of the arms has an overhang 278. The four arms, in this exemplary embodiment, form a quasi-chamber 280 into which tissue growth or bone growth material may be placed to facilitate fusion. Also, the plurality of arms 206, as well as the first and second 202, 204 extension may include surface texturing, roughing, plasma coating, or the like to facilitate tissue and bone growth. Further, as mentioned above, more or less arms 206 are possible such as, for example, a midline arm $206m_1$ and $206m_2$ as shown in phantom. Additionally, the posterior arms $206p_1$ and $206p_2$ comprise a main body 362 from which the overhang 278 extends. The anterior arms $206a_1$ and $206a_2$ have an anterior wall member 364 from which the overhang 278 extends. The anterior wall member may comprise different heights, as shown in phantom, from about two (2) millimeters to about eight (8) millimeters. The anterior wall members 364 together form a larger anterior wall to facilitate retention of any tissue or bone growth material placed in quasi-chamber 280. As can be appreciated, the smaller anterior wall members 364 of approximately 2 mm would be used in smaller applications of the present technology, such as, for the cervical spine space; whereas, the larger anterior wall members 364 of approximately 8 mm would be used in larger applications of the present technology, such as the lumbar spine space. The anterior wall members 364 could have heights of three (3), four (4), five (5), six (6), seven (7) or even up to about ten (10) millimeters depending on the application. As can be appreciated, in the compact state, the anterior wall members substantially abut or overlap. As the implant is expanded or distracted, the anterior wall members slidingly move against each other to the expanded state.

Figure 29:
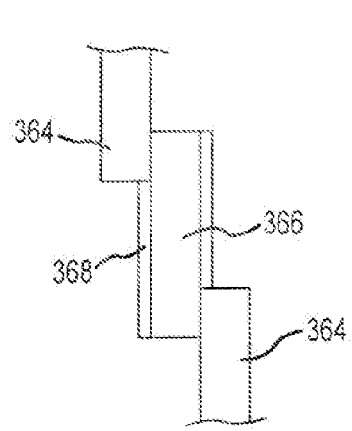
Figure 30:
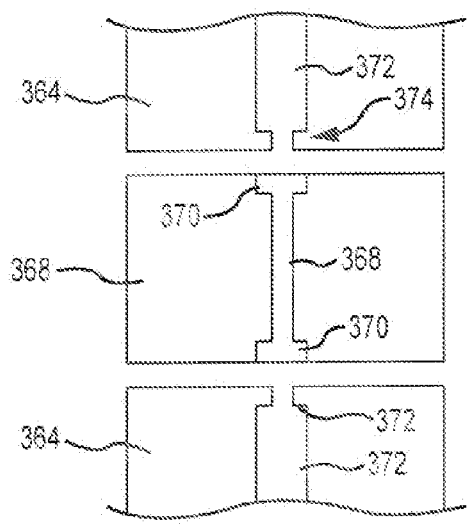

Alternatively, as shown in FIG. 29, a floating wall 366 may be provided between the anterior wall members 364. The floating wall 366 is slidingly and moveably coupled to one or both of the anterior wall members 364. Additionally, while only one floating wall 366 is shown, multiple floating walls 366 may be layered to provide different extension lengths. In one exemplary embodiment, the floating wall 366 may have a tongue 368 with a flare 370 that engages a groove 372 and stop 374 on the anterior wall members 364, as shown partially exploded in FIG. 30.

Figure 31:
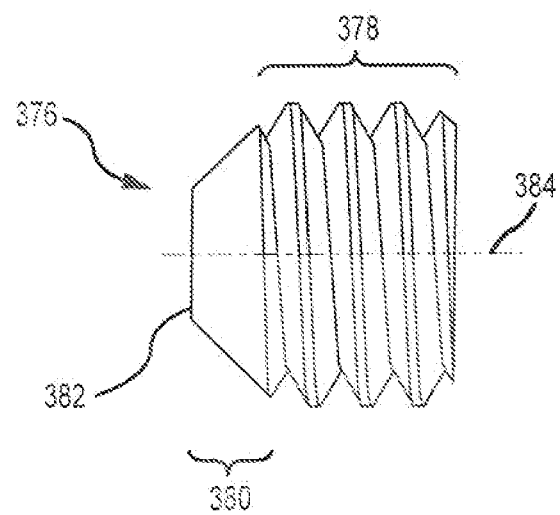
FIGS. 31-33 are view of a screw associated with the implant consistent with the technology of the application.
Figure 32:
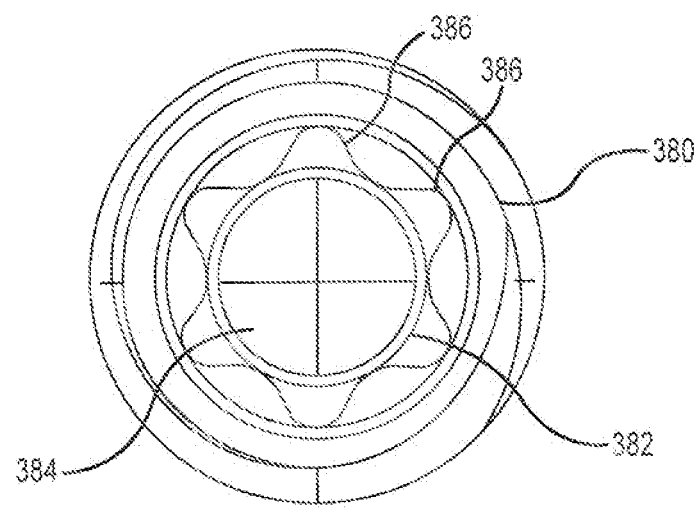
Figure 33:
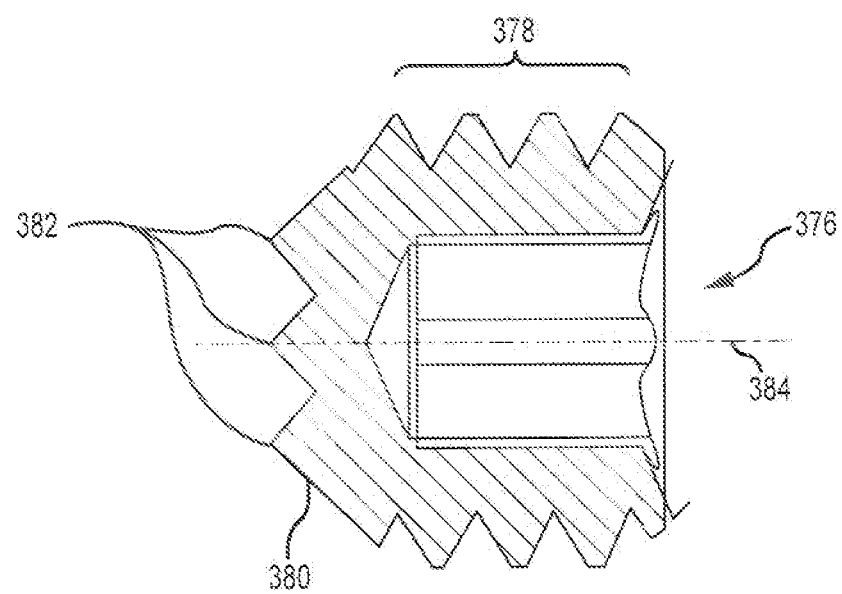

As mentioned above, once distracted, the first and third parts 208, 300 may be locked to the male members 240, 328, of the second and fourth parts 210, 302 of the implant 200. In the exemplary embodiment provided, set screws 268, 314 are threaded into threaded bores 224, 314 respectively. An exemplary set screw 376 is shown in FIGS. 31 and 32. The set screw 376 has a threaded body 378 that cooperatively engages the threads of threaded bores 224, 314. The set screw 376 also has, in this exemplary embodiment, a non-threaded tip 380 that terminates in an edge 382, which is circular in this embodiment. The set screw 376 may have an internal bore 384 adapted to engage a driver (not shown). The bore 384 may have a number of undulations 386 or the like to facilitate engagement with the driver, such as a hex driver, hexalobular, star driver, or the like. The set screw 376 is shown in cross-section in FIG. 33. The edge 382 of the set screw 376 engages the surface texturing 243 on the male members 240, 328 to form a cup point connection as is generally known in the industry. To facilitate the cup point connection, the surface texturing may be scooped, or dual crescent, shaped to match the curvature of the edge 382.

Some exemplary tools and instruments usable with the implant 200 will be shown and described with reference to the remaining FIGS. While some tools are specifically shown, it should be understood that other and different tools may be used to accomplish many of the functions of the technology of the present application.

Figure 34:
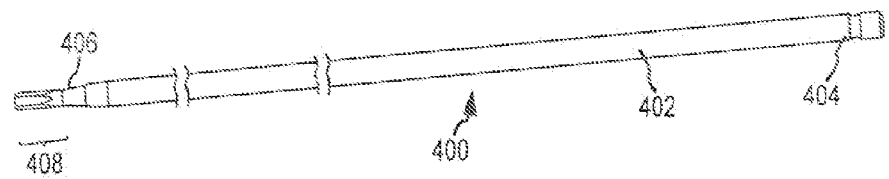

A driver 400 may be provided as shown in FIG. 34. The driver 400 has a shaft 402 with a proximal end 404 and a distal end 406. The distal end 406 may terminate in a tip 408, such as, for example, a conventional hex or star shape, to cooperatively engage the bore 384 of the set screws. The proximal end 402 may be sized and designed to facilitate rotation of the driver by hand.

Figure 35:
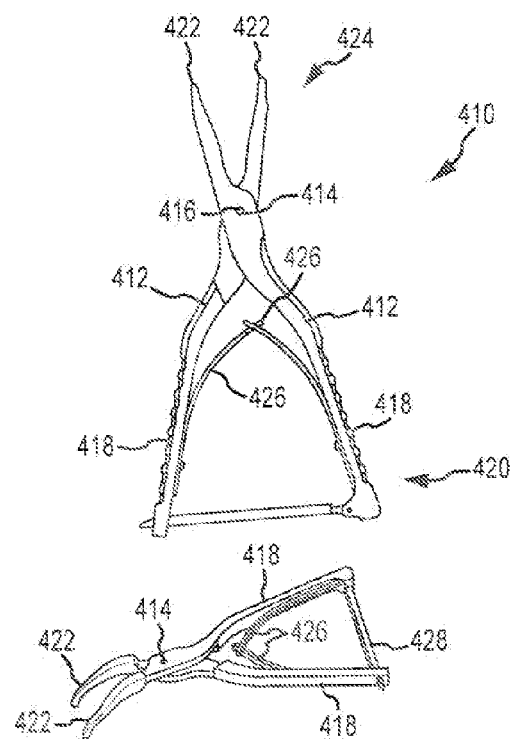
Figure 38:
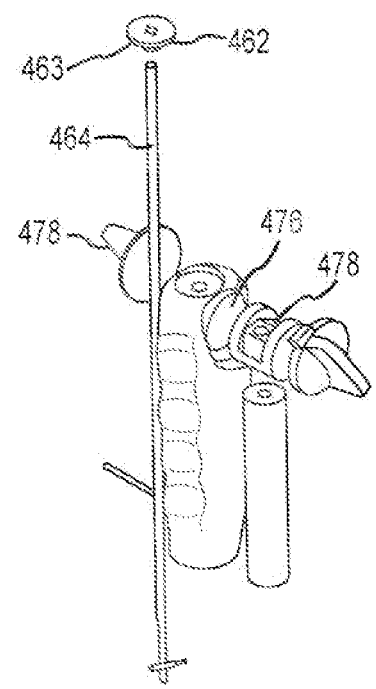

A compressor 410 may be provided as shown in FIG. 35. The compressor 410 includes two members 412 pivotally connected. The pivotal connection 414 may comprise a pin 416, or axle, coupling the two members 412 together. Each of the members 412 has a handle or grip 418 at a proximal end 420 of the compressor 410 and a tip 422 at the distal end 424 of the compressor. The grips are biased apart by springs 426, such as, for example, leaf springs. When the grips 418 are compressed together against the springs 426, the tips 422 compress the first and second extensions 202, 204 together. A lock bar 428 maintains the grips 418 in the compressed state until the lock bar is manually lifted, at which time the springs open the compressor 410. The tips may be textured to facilitate gripping the first and second extensions. As can be appreciated, multiple compressors 410 may be required for smooth compression of the multiple parts of the first and second extensions.

With reference now to FIGS. 36 and 37, a combination inserter and expander tool 450 is provided. FIG. 36 shows a view of the tool 450 and FIG. 37 shows a cross-sectional view of the tool 450. The tool 450 has a proximal end 452 with an enlarged grip 454 to improve the surgeon's ability to grip the tool 450; however, the grip 454 does not need to be enlarged. The tool also has a distal end 456 for connection to the implant 200, as will be explained further below. The distal end 456 is adapted to be moved from outside the body of a patient to the surgical site. The handle or grip 454 is connected to a shaft nut 462 that is connected to the shaft 460. The shaft 460 terminates in a tip 458.

The grip 454 terminates at an end 461 that may include a display face 462. The display face 462 may have indicia 463 corresponding to the distraction to be provided to the spinous processes. The display face 462 and indicia are coupled to a proximal end of a drive axle 464. The drive axle 464 extends along a longitudinal axis 466 of the tool 450 from the proximal end to the tip 458 at the distal end 456. The proximal end of the drive axle 464 is coupled to a worm gear 468 such that rotation of the worm gear 468 rotates the drive axle 464. The worm gear 468 meshes with a threaded portion 470 (worm) of a transverse axle 472 having a transverse axis 474 that is perpendicular to the longitudinal axis 466. The transverse axle 474 extends through a bore 476 towards the end of the grip 454. As shown, each end of the transverse axle 474 terminates in rotatable tabs 478, which may be thumb wheels or the like. Rotation of the tabs 478 causes the worm gear 468 to rotate, which in turn rotates the drive axle 464 and the display face 462. A pinion gear 480 contained in the tip 458 has teeth 482 that mesh with the indentations 238 or rack cutouts to drive the male member into or out of the associated female member.

Figure 39:
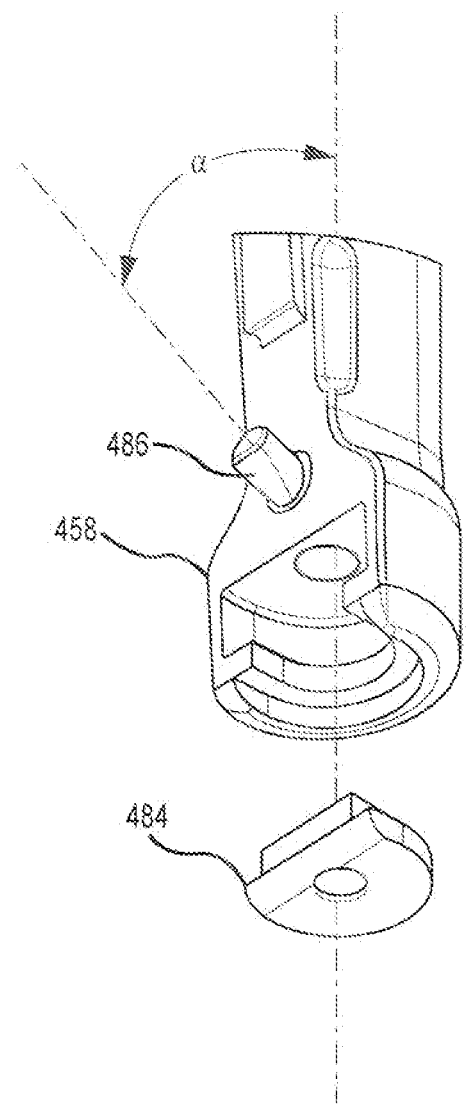

FIG. 39 shows the tip 458 in more detail without the pinion gear 480 or the drive axle 464. The tip 458 may include a removable cap 484 such that the pinion gear 480 may be replaced or refurbished as required. The tip 458 further has an engagement detent 486. The engagement detent 486 couples to an inserter tool bore 488 (FIG. 10A) such that the tool 450 may be releasably coupled to the implant 200. While the engagement detent 486 may form a 90° angle with respect to the longitudinal axis 466, the engagement detent 486 may be angled slightly towards the proximal end of the tool 450 such that the engagement detent 486 extends at an acute angle a in the posterior direction. The acute angle a provides a better connection between the tool 450 and the implant 200.

Figure 40:
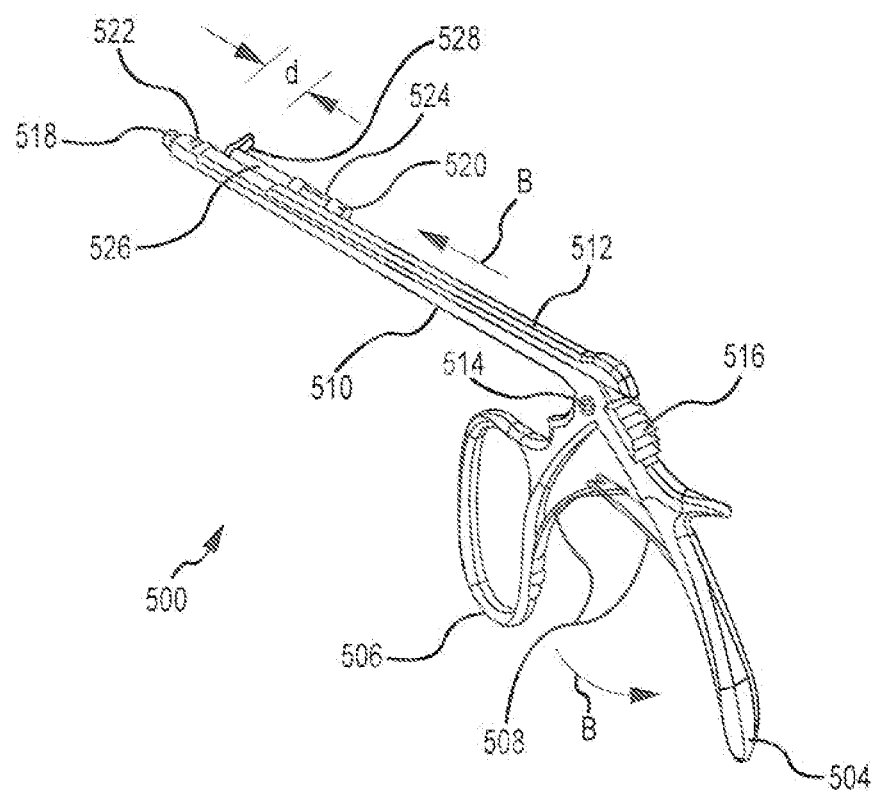

In certain applications, the implant 200 may be partially assembled exterior to a patient prior to implantation. In other cases, the first extension 202 and the plurality of arms 206 may be implanted first and the second extension 204 inserted subsequent to the arms being extended through the interspinous space. To facilitate movement of the second extension 204, a second extension inserter 500 is provided as shown in FIG. 40. Inserter 500 includes a pistol grip 502 comprising a post 504 and a movable trigger 506. The moveable trigger 506 is biased away from the post 504 by a pair of cooperating springs 508, such as, for example, leaf springs. Extending along a longitudinal axis is a stationary shaft 510 coupled to post 504. The shaft 510 is called the stationary shaft as it does not move relative to the post 504. A movable shaft 512 is slidingly coupled to the stationary shaft and the trigger 506. Moving the trigger 506 towards the post 504 in a direction A about the pivot axle 514 causes the movable shaft 512 to move in a direction B relative to the stationary shaft 510. A lock 516, such as the shown thumb lock, may be moved into place to maintain the tool in the grip position against the springs 508.

The movable shaft 512 has a tip 522 that extends into the posteriorly extending tool port 348, which may bias the spring arm 360 to disengage the plunger 352 from posterior arm 206$p_2$ and allow movement of the second extension 204 away from the first extension 202. In this manner, the second extension 204 may be translated relative to the first extension 202 without ratcheting. The ratchets may then be reengaged by removing tip 522 from port 348 to help secure the second extension 204 at the desired time or location. The stationary shaft 510 has a protrusion 518 that engages an opening or detent on the lateral surface of the second extension 204 to help retain shaft 510 thereto.

A housing 520 is coupled to the movable shaft 512 a distance d along the movable shaft 512 from a tip 522. The housing 520 contains a compression member 524, such as a spring. Extending from the housing 520 toward the tip 522 is an arm 526, wherein the spring and arm may be considered a spring loaded arm. The arm 526 has a flanged gripping surface 528 to provide a frictional gripping force when the trigger 506 is moved towards the post 504 such that the tool 500 can grip the second extension 204.

As herein, "about" refers to a degree of deviation. based on experimental error typical for the particular property identified. The latitude provided the term "about" will depend on the specific context and particular property and can be readily discerned. by those skilled in the art. The term "about" is not intended to either expand or limit the degree of equivalents which may otherwise be afforded a particular value. Further, unless otherwise stated, the term "about" shall expressly include "exactly," consistent with the discussions regarding ranges and numerical data. Concentrations, amounts, and other numerical data may he expressed or presented herein in a range format. It is to be understood that such a range format is used merely for convenience and brevity and, thus, should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5; etc. This same principle applies to ranges reciting only one numerical value. Furthermore, such an interpretation should apply regardless of the breadth of the range or the characteristics being described.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the present invention.

Numerous other changes may be made which will readily suggest themselves to those skilled in the art and which are encompassed in the spirit of the disclosure.

We claim:

1. An apparatus comprising:
   a first extension having a lateral facing side and a medial facing side, the medial facing side adapted to reside proximate a first surface of a spinous process, the first extension defines a horizontal axis that extends substantially perpendicular to the medial facing side;
   the first extension including a first part comprising a first male member extending in an inferior direction along a first vertical axis and a first female member extending in a superior direction along a second vertical axis, the first female member defining a first socket;
   the first extension including a second part comprising a second male member extending in a superior direction along a third vertical axis and a second female member extending in an inferior direction along a fourth vertical axis, the second female member defining a second socket, wherein the third vertical axis is substantially aligned with the second vertical axis such that the second male member is telescopically received in the first socket and the fourth vertical axis is substantially aligned with the first vertical axis such that the first male member is telescopically received in the second socket;

a plurality of arms cantilevered from the medial facing side of the first extension and extending a distance along the horizontal axis, at least a first arm of the plurality of arms cantilevered from the first part and at least a second arm of the plurality of arms cantilevered from the second part, the first and second arms forming a chamber extending therebetween along the horizontal axis;

the first and second male members and the first and second female members of the first extension permitting movement between a compact state where the first arm and the second arm form a first height and a distracted state where the first arm and the second arm form a second height that is greater than the first height;

a second extension comprising a lateral facing side and a medial facing side, the medial facing side adapted to reside proximate a second surface of the spinous process opposite the first surface;

the second extension including a third part and a fourth part that are movable with the first part and the second part from the compact state to the distracted state, the third part comprising a third female member extending along a fifth vertical axis to define a third socket and the fourth part comprising a third male member extending along a sixth vertical axis, wherein the fifth vertical axis is substantially aligned with the sixth vertical axis such that the third male member is telescopically received in the third socket; and the third part defining a first cavity sized to slidingly receive the first arm and the fourth part defining a second cavity sized to slidingly receive the second arm, wherein the first and second cavities are offset from the fifth and sixth vertical axes respectively to provide access to the chamber from the lateral facing side of the second extension when the third and fourth parts are positioned in both the distracted state and the compact state.

2. The apparatus of claim 1, wherein the plurality of arms comprises a first anterior arm and a first posterior arm coupled to the first part and a second anterior arm and a second posterior arm coupled to the second part.

3. The apparatus of claim 2, wherein at least one of the first and second anterior arms and the first and second posterior arms comprise an overhang.

4. The apparatus of claim 2, wherein each of the first and second anterior arms comprise an overhang extending horizontally along the distance of the first and second anterior arms towards the first and second posterior arms respectively and wherein each of the first and second posterior arms comprise an overhang extending horizontally along the distance of the first and second posterior arms towards the first and second anterior arms respectively such that a material promoting tissue growth may be held in the chamber by the overhangs of the first anterior and posterior arms and the overhangs of the second anterior and posterior arms.

5. The apparatus of claim 4, wherein the first anterior arm comprises a first wall member extending from the first anterior arm towards the second anterior arm, and the second anterior arm comprises a second wall member extending from the second anterior arm towards the first anterior arm.

6. The apparatus of claim 5, wherein the first wall member and the second wall member are configured to slidingly move with respect to each other as the first extension moves between the compact state and the distracted state.

7. The apparatus of claim 1, wherein the chamber is adapted to contain material to promote tissue growth.

8. The apparatus of claim 1, wherein the first male member comprises a plurality of indentations and the lateral facing side of the second part comprises a window adapted to provide access to the plurality of indentations.

9. The apparatus of claim 1, wherein the first part comprises an anterior facing side and a posterior facing side, wherein the first male member resides on the anterior facing side and the first female member resides on the posterior facing side, and further comprising a bore extending from the posterior facing side to the first socket.

10. The apparatus of claim 9, further comprising a fastener operatively coupled to the bore such that the fastener extends through the bore and releasably couples to the second male member, whereby the first part and the second part are locked in place with respect to each other.

11. The apparatus of claim 10, wherein the fastener comprises a threaded set screw and the bore comprises a threaded bore, and wherein the second male member comprises surface texturing on a posterior face to cooperatively engage a leading edge of the set screw.

12. The apparatus of claim 11, wherein the surface texturing is crescent shaped.

13. The apparatus of claim 1, wherein the medial facing side comprises at least one fastener extending in a direction along the horizontal axis and adapted to operatively couple to a spinous process.

14. The apparatus of claim 1, wherein the first and second sockets extend completely through the first and second female members.

15. The apparatus of claim 1, wherein the third part comprises a first anchor extending in an inferior direction and wherein the fourth part comprises a second anchor extending in a superior direction whereby the first and second cavities are formed in part by the first and second anchors and where the first and second anchors are offset from the fifth and sixth axes respectively and are spaced from one another when the third and fourth parts are positioned in both the distracted state and the compact state.

16. The apparatus of claim 15, wherein the first and second anchors are spaced from the third female member and the third male member by central portions of the third and fourth parts respectively and comprise a post terminating in a flanged surface.

17. The apparatus of claim 16, wherein the first cavity is a first interior cavity and the second cavity is a second interior cavity and the first and second anchors further form first and second exterior cavities.

18. The apparatus of claim 1, wherein the second extension is releasably and slidingly coupled to the plurality of arms.

19. The apparatus of claim 18, wherein the fourth part comprises:
a first member comprising a port in communication with the second cavity; and
a movable plunger disposed in said port wherein the plunger is movable from a first position where the plunger engages the second arm to a second position where the plunger disengages the second arm.

20. The apparatus of claim 19, wherein the movable plunger is biased to the first position with a spring.

21. The apparatus of claim 19, wherein the plunger comprises a first plurality of teeth that engage a second plurality of teeth on the second arm.

22. An interspinous implant comprising:
a first extension having a lateral facing side and a medial facing side, the medial facing side adapted to reside proximate a first surface of a spinous process, the first extension defines a horizontal axis that extends substantially perpendicular to the medial facing side;
the first extension including a first part comprising a first male member extending in an inferior direction along a first vertical axis and a first female member extending in a superior direction along a second vertical axis, the first female member defining a first socket;
the first extension including a second part comprising a second male member extending in a superior direction along a third vertical axis and a second female member extending in an inferior direction along a fourth vertical axis, the second female member defining a second socket, wherein the third vertical axis is substantially aligned with the second vertical axis such that the second male member is telescopically received in the first socket and the fourth vertical axis is substantially aligned with the first vertical axis such that the first male member is telescopically received in the second socket;
a plurality of arms cantilevered from the medial facing side of the first extension and extending a distance along the horizontal axis, the plurality of arms including a first anterior arm and a first posterior arm cantilevered from the first part and a second anterior arm and a second posterior arm cantilevered from the second part;
a second extension comprising a lateral facing side and a medial facing side, the medial facing side adapted to reside proximate a second surface of the spinous process opposite the first surface;
the second extension including a third part comprising a first anchor at least partially defining a first interior cavity sized to slidingly receive the first anterior arm and a first exterior cavity sized to slidingly receive the first posterior arm;
the second extension including a fourth part comprising a second anchor at least partially defining a second interior cavity sized to slidingly receive the second anterior arm and a second exterior cavity sized to slidingly receive the second posterior arm; and
the plurality of arms and the first and second anchors having a tongue and groove arrangement where the plurality of arms have a substantially L-shaped cross-section and where the first and second anchors have a substantially T-shaped cross-section that at least partially defines the first and second interior cavities and the first and second exterior cavities.

\* \* \* \* \*